(12) United States Patent
Galipeau et al.

(10) Patent No.: US 8,283,449 B2
(45) Date of Patent: Oct. 9, 2012

(54) INTERLEUKIN-2/SOLUBLE TGA-BETA TYPE II RECEPTOR B CONJUGATES AND METHODS AND USES THEREOF

(76) Inventors: Jacques Galipeau, Atlanta, GA (US); Claudia Penafuerte-Diaz, Montreal (CA)

( * ) Notice: Subject to any disclaimer, the term of this patent is extended or adjusted under 35 U.S.C. 154(b) by 0 days.

(21) Appl. No.: 12/973,400

(22) Filed: Dec. 20, 2010

(65) Prior Publication Data

US 2011/0150828 A1 Jun. 23, 2011

Related U.S. Application Data

(63) Continuation-in-part of application No. PCT/CA2009/000841, filed on Jun. 19, 2009.

(60) Provisional application No. 61/074,369, filed on Jun. 20, 2008.

(51) Int. Cl.
*C07K 1/00* (2006.01)
*C07K 14/00* (2006.01)

(52) U.S. Cl. .................................. 530/351; 530/402

(58) Field of Classification Search .................. None
See application file for complete search history.

(56) References Cited

U.S. PATENT DOCUMENTS

| 4,401,756 | A | 8/1983 | Gillis |
| 4,448,879 | A | 5/1984 | Fabricius et al. |
| 4,464,355 | A | 8/1984 | Fabricius et al. |
| 4,490,289 | A | 12/1984 | Stern |
| 4,518,584 | A | 5/1985 | Mark et al. |
| 4,778,879 | A | 10/1988 | Mertelsmann et al. |
| 4,925,919 | A | 5/1990 | Mertelsmann et al. |
| 6,001,969 | A | 12/1999 | Lin et al. |
| 6,008,011 | A | 12/1999 | Lin et al. |
| 6,046,157 | A | 4/2000 | Lin et al. |
| 6,201,108 | B1 | 3/2001 | Lin et al. |
| 2005/0203022 | A1 | 9/2005 | Gotwals et al. |
| 2007/0212703 | A1* | 9/2007 | Stemmer et al. ........... 435/6 |

FOREIGN PATENT DOCUMENTS

| EP | 1925626 | 5/2008 |
| WO | 9848024 | 10/1998 |
| WO | 03035105 | 5/2003 |
| WO | 2009152610 | 12/2009 |

OTHER PUBLICATIONS

Bowie et al, 1990, Science 247:1306-1310.*
Wells, 1990, Biochemistry 29:8509-8517.*
Ngo et al., 1994, The Protein Folding Problem and Tertiary Structure Prediction, Merz et al., eds, Birkhauser, Boston, pp. 433-506.*
Wang et al (2001. J. Biol Chem. 276:49213-49220.*
Penafuerte-Diaz, C.A. et al., "Chimeric fusokines borne of the marriage of the TGFβ receptor II ectodomain and pro-inflammatory cytokines IL2 and GMCSF for breast cancer immunotherapy". Cytokine, Sep. 2008, vol. 43, No. 3, p. 311.
Penafuerte-Diaz, C. et al., "TGFβ secreted by B16 melanoma antagonizes cancer gene immunotherapy bystander effect". Cancer Immunology, Immunotherapy. Aug. 2008 (published online Jan. 24, 2008), vol. 57, No. 8, pp. 1197-1206.

* cited by examiner

*Primary Examiner* — Shulamith H Shafer

(57) ABSTRACT

A conjugate protein comprising an IL-2 and a soluble TGF-beta type II receptor type B and its use in cancer immunotherapy are described.

4 Claims, 15 Drawing Sheets

Figure 1

A mIL-2

MYSMQLASCVTLTLVLLVNSAPTSSSTSS
STAEAQQQQQQQQQQQQHLEQLLMDLQ
ELLSRMENYRNLKLPRMLTFKFYLPKQA
TELKDLQCLEDELGPLRHVLDLTQSKSFQ
LEDAENFISNIRVTVVKLKGSDNTFECQF
DDESATVVDFLRRWIAFCQSIIST

ASATGLRSR Linker msTbRIIb

RIASTIPPHVPKSDVEMEAQKDASIHLSCN
RTIHPLKHFNSDVMASDNGGAVKLPQLC
KFCDVRLSTCDNQKSCMSNCSITAICEKP
HEVCVAVWRKNDKNITLETVCHDPKLTY
HGFTLEDAASPKCVMKEKKRAGETFFMC
ACNMEECNDYIIFSEEYTTSSPDLLLVIIQ
VTDPL

B

1- mFIST 2- sTβRIIb

3- Non transfected cells (NT)

C

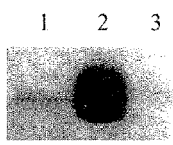

1- Isotype + TGFβ

2- mFIST + TGFβ

3- Non transfected cells (NT)

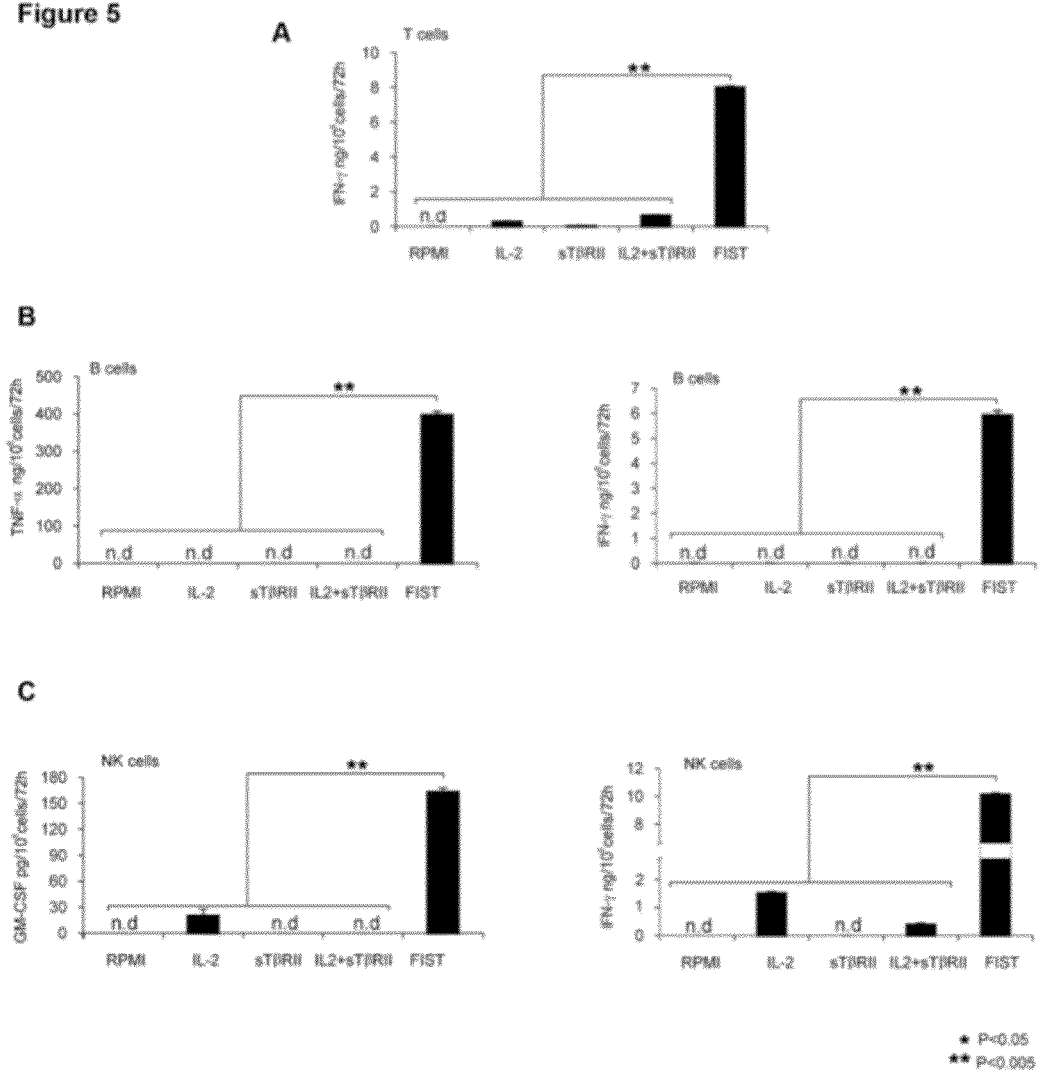

Figure 6
A
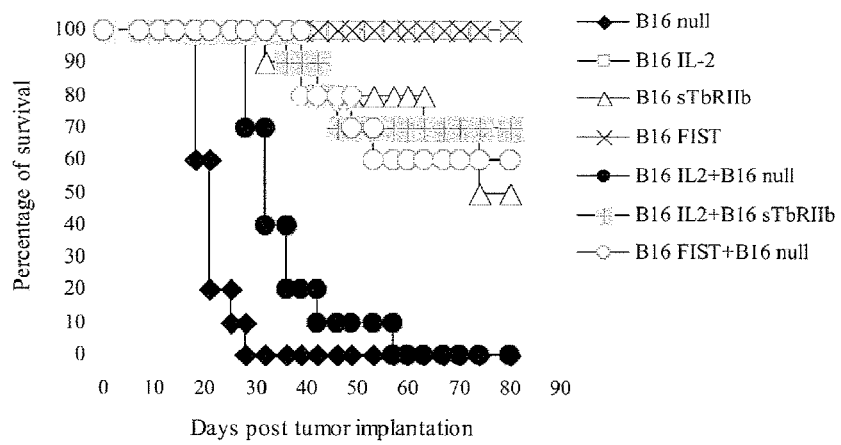
B
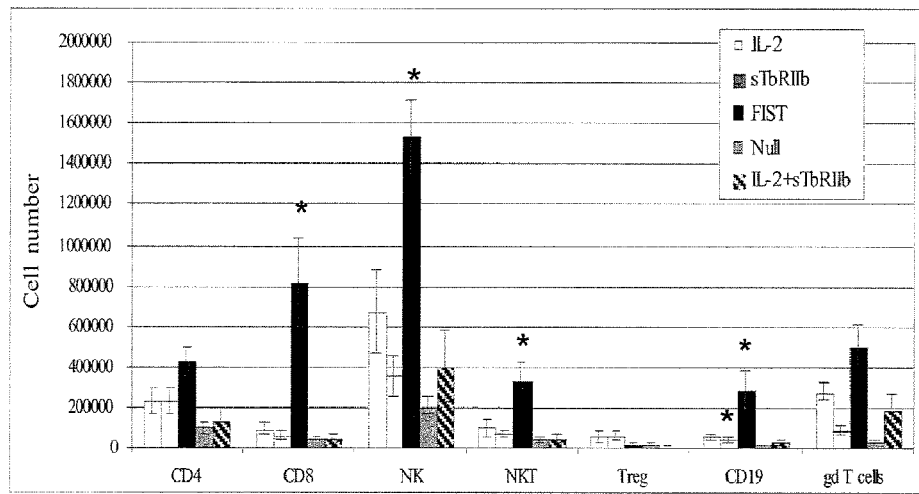
C
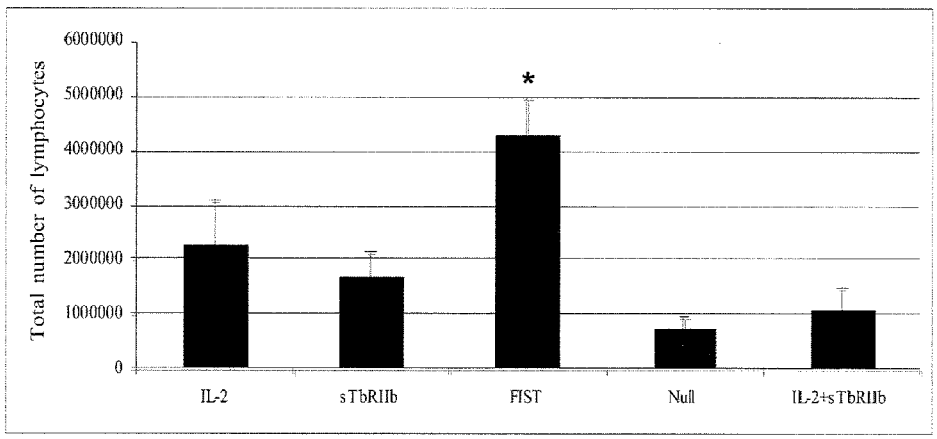

Figure 8

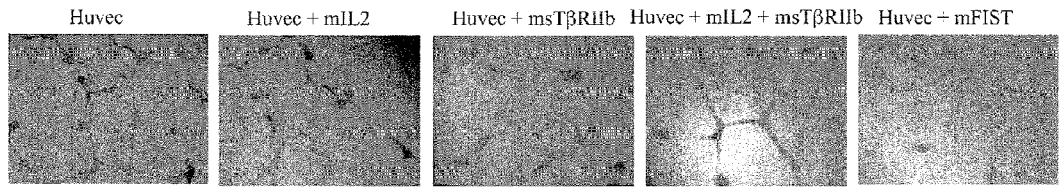

| Huvec | Huvec + mIL2 | Huvec + msTβRIIb | Huvec + mIL2 + msTβRIIb | Huvec + mFIST |
|---|---|---|---|---|
| Polygons number: 16 | Polygons number: 11 | Polygons number: 9 | Polygons number: 5 | Polygons number: 0 |
| Score: 8 | Score: 8 | Score: 5 | Score: 5 | Score: 0 |
| A: 3 | A: 3 | A: 1 | A: 1 | A: 0 |
| B: 2 | B: 2 | B: 3 | B: 2 | B: 0 |
| C: 3 | C: 3 | C: 3 | C: 2 | C: 0 |

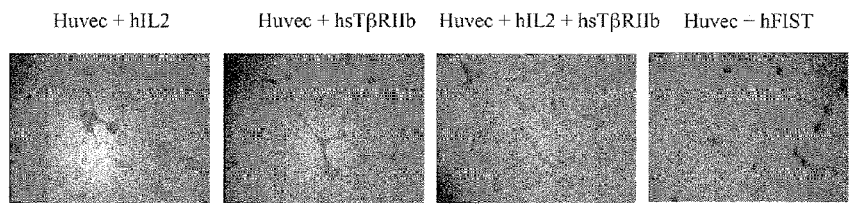

| Huvec + hIL2 | Huvec + hsTβRIIb | Huvec + hIL2 + hsTβRIIb | Huvec + hFIST |
|---|---|---|---|
| Polygons number: 6 | Polygons number: 6 | Polygons number: 12 | Polygons number: 0 |
| Score: 7 | Score: 6 | Score: 8 | Score: 0 |
| A: 1 | A: 1 | A: 3 | A: 0 |
| B: 3 | B: 2 | B: 2 | B: 0 |
| C: 3 | C: 3 | C: 3 | C: 0 |

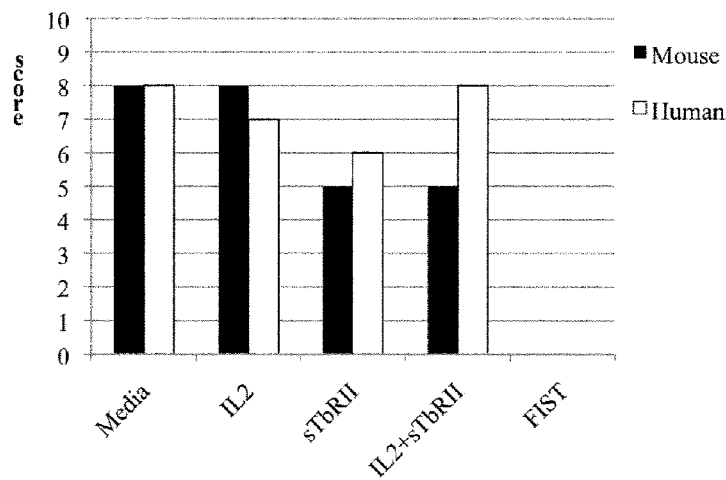

Figure 10
A
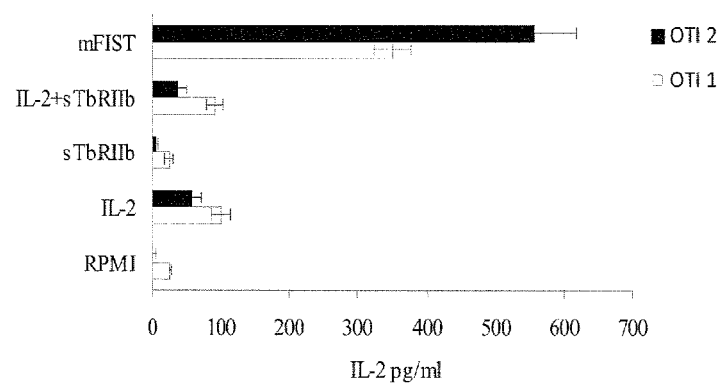
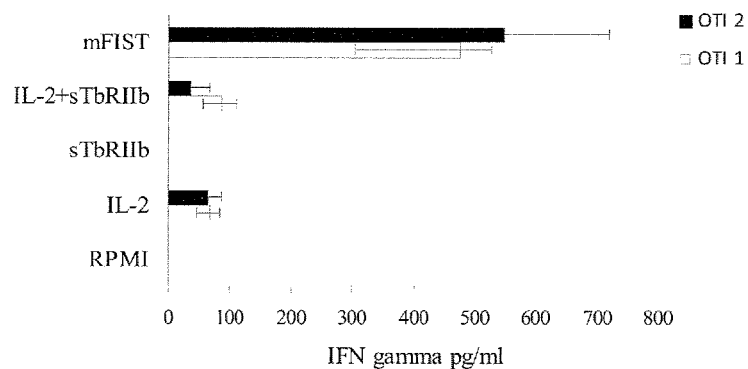
B
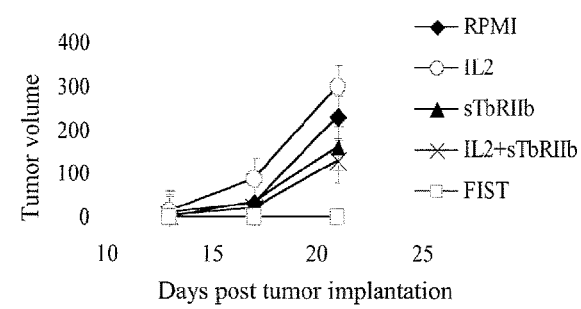
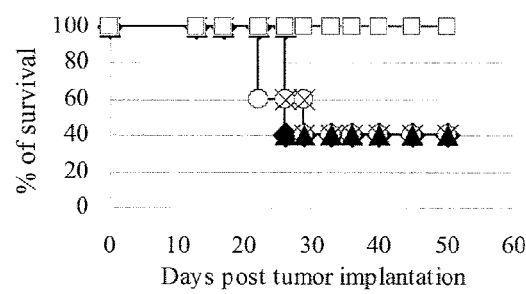

Figure 11

A hIL-2
MYRMQLLSCIALSLALVTNSAPTSSSTKKTQ
LQLEHLLLDLQMILNGINNYKNPKLTRMLT
FKFYMPKKATELKHLQCLEEELKPLEEVLN
LAQSKNFHLRPRDLISNINVIVLELKGSETTF
MCEYADETATIVEFLNRWI
LRG (Linker)
hsTβRIIb
LWPLIIIVLWTRIASTIPPHVQKSDVEMEAQ
KDEIICPSCNRTAHPLRHINNDMIVTDNNGA
VKFPQLCKFCDVRFSTCDNQKSCMSNCSITS
ICEKPQEVCVAVWRKNDENITLETVCHDPK
LPYHDFILEDAASPKCIMKEKKKPGETFFMC
SCSSDECNDNIIFSEEYNTSNPDFWEPVQE

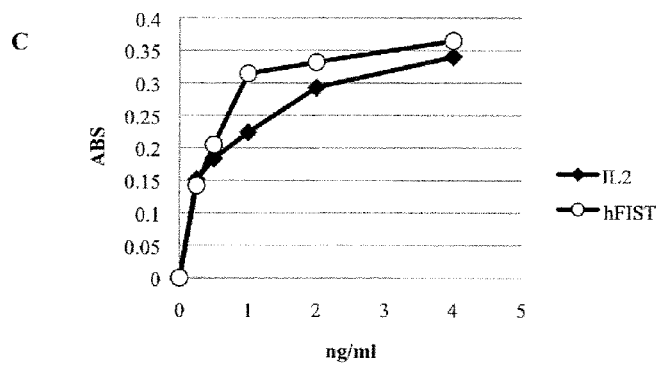

B

C 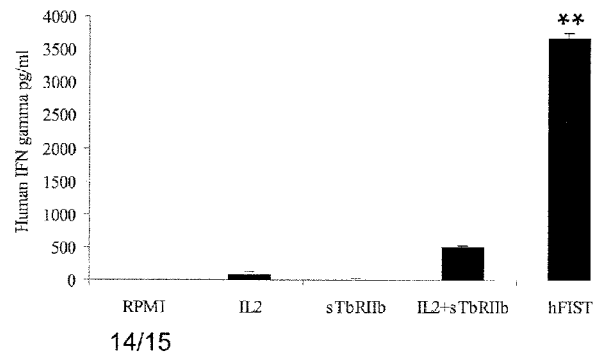

A
hFIST v.1
MYRMQLLSCIALSLALVTNSAPTSSSTKKTQLQLEHLLLDLQMILNGINNYKN
PKLTRMLTFKFYMPKKATELKHLQCLEEELKPLEEVLNLAQSKNFHLRPRDLI
SNINVIVLELKGSETTFMCEYADETATIVEFLNRWILRGLWPLHIVLWTRIASTI
PPHVQKSDVEMEAQKDEIICPSCNRTAHPLRHINNDMIVTDNNGAVKFPQLCKFCDVRF
STCDNQKSCMSNCSITSICEKPQEVCVAVWRKNDENITLETVCHDPKLPYHDFILEDAAS
PKCIMKEKKKPGETFFMCSCSSDECNDNIIFSEEYNTSNPEFWEPVQEN (SEQ ID NO:4)

B
hFIST v.2
MYRMQLLSCIALSLALVTNSAPTSSSTKKTQLQLEHLLLDLQMILNGINNYKN
PKLTRMLTFKFYMPKKATELKHLQCLEEELKPLEEVLNLAQSKNFHLRPRDLI
SNINVIVLELKGSETTFMCEYADETATIVEFLNRWIRIASTIPPHVQKSDVEMEAQKDEIIC
PSCNRTAHPLRHINNDMIVTDNNGAVKFPQLCKFCDVRFSTCDNQKSCMSNCSITSICEK
PQEVCVAVWRKNDENITLETVCHDPKLPYHDFILEDAASPKCIMKEKKKPGETFFMCSC
SSDECNDNIIFSEEYNTSNPEFWEPVQE (SEQ ID NO:8)

C
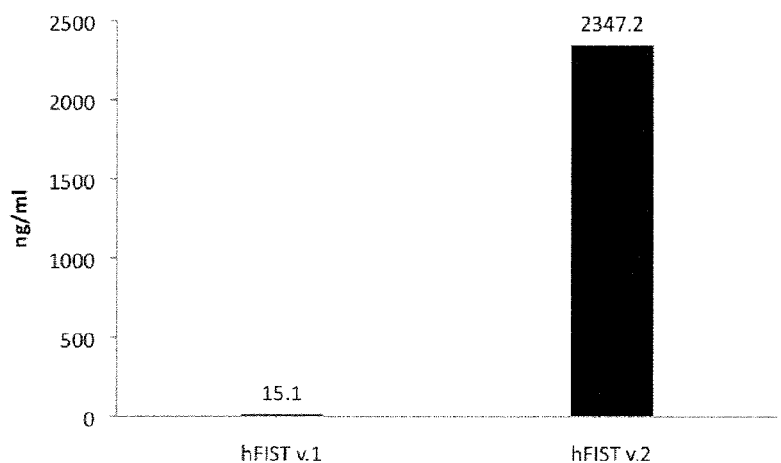

SEQUENCE LISTING

```
<160> NUMBER OF SEQ ID NOS: 8

<210> SEQ ID NO 1
<211> LENGTH: 1061
<212> TYPE: DNA
<213> ORGANISM: Artificial Sequence
<220> FEATURE:
<223> OTHER INFORMATION: DNA Sequence of mouse IL2/sT(beta)RII fusion
      protein

<400> SEQUENCE: 1
atgtacagca tgcagctcgc atcctgtgtc acattgacac ttgtgctcct tgtcaacagc      60
gcacccactt caagctccac ttcaagctct acagcggaag cacagcagca gcagcagcag     120
cagcagcagc agcagcagca cctggagcag ctgttgatgg acctacagga gctcctgagc     180
aggatggaga attacaggaa cctgaaactc cccaggatgc tcaccttcaa attttacttg     240
cccaagcagg ccacagaatt gaaagatctt cagtgcctag aagatgaact tggacctctg     300
cggcatgttc tggatttgac tcaaagcaaa agctttcaat tggaagatgc tgagaatttc     360
atcagcaata tcagagtaac tgttgtaaaa ctaaagggct ctgacaacac atttgagtgc     420
caattcgatg atgagtcagc aactgtggtg gactttctga ggagatggat agccttctgt     480
caaagcatca tctcaacagc tagcgctacc ggactcagat ctcgacgcat cgccagcacg     540
atcccgccgc acgttcccaa gtcggatgtg gaaatggaag cccagaaaga tgcatccatc     600
cacctaagct gtaataggac catccatcca ctgaaacatt ttaacagtga tgtcatggcc     660
agcgacaatg gcggtgcggt caagcttcca cagctgtgca gtttttgcga tgtgagactg     720
tccacttgcg acaaccagaa gtcctgcatg agcaactgca gcatcacggc catctgtgag     780
aagccgcatg aagtctgcgt ggccgtgtgg aggaagaacg acaagaacat tactctggag     840
acggtttgcc acgaccccaa gctcacctac cacggcttca ctctggaaga tgccgcttct     900
cccagtgtgt catgaagga aaagaaaagg gcgggcgaga cttcttcat gtgtgcctgt      960 aacatggaag agtgcaacga ttacatcatc ttttcggaag aatacaccac cagcagtccc    1020
gacctgttgt tggtcattat ccaagtgacg gatccccttt g                        1061

<210> SEQ ID NO 2
<211> LENGTH: 353
<212> TYPE: PRT
<213> ORGANISM: Artificial Sequence
<220> FEATURE:
<223> OTHER INFORMATION: Amino-acid sequence of mouse IL-2/sT(beta)RII
      fusion protein

<400> SEQUENCE: 2
```

```
Met Tyr Ser Met Gln Leu Ala Ser Cys Val Thr Leu Thr Leu Val Leu
1               5                   10                  15
Leu Val Asn Ser Ala Pro Thr Ser Ser Thr Ser Ser Thr Ala
            20                  25                  30
Glu Ala Gln Gln Gln Gln Gln Gln Gln Gln Gln Gln His Leu
            35                  40                  45
Glu Gln Leu Leu Met Asp Leu Gln Glu Leu Leu Ser Arg Met Glu Asn
50                  55                  60
Tyr Arg Asn Leu Lys Leu Pro Arg Met Leu Thr Phe Lys Phe Tyr Leu
65                  70                  75                  80
Pro Lys Gln Ala Thr Glu Leu Lys Asp Leu Gln Cys Leu Glu Asp Glu
                85                  90                  95
Leu Gly Pro Leu Arg His Val Leu Asp Leu Thr Gln Ser Lys Ser Phe
            100                 105                 110
Gln Leu Glu Asp Ala Glu Asn Phe Ile Ser Asn Ile Arg Val Thr Val
            115                 120                 125
Val Lys Leu Lys Gly Ser Asp Asn Thr Phe Glu Cys Gln Phe Asp Asp
130                 135                 140
Glu Ser Ala Thr Val Val Asp Phe Leu Arg Arg Trp Ile Ala Phe Cys
145                 150                 155                 160
Gln Ser Ile Ile Ser Thr Ala Ser Ala Thr Gly Leu Arg Ser Arg Arg
                165                 170                 175
Ile Ala Ser Thr Ile Pro Pro His Val Pro Lys Ser Asp Val Glu Met
            180                 185                 190
Glu Ala Gln Lys Asp Ala Ser Ile His Leu Ser Cys Asn Arg Thr Ile
            195                 200                 205
His Pro Leu Lys His Phe Asn Ser Asp Val Met Ala Ser Asp Asn Gly
210                 215                 220
Gly Ala Val Lys Leu Pro Gln Leu Cys Lys Phe Cys Asp Val Arg Leu
225                 230                 235                 240
Ser Thr Cys Asp Asn Gln Lys Ser Cys Met Ser Asn Cys Ser Ile Thr
                245                 250                 255
Ala Ile Cys Glu Lys Pro His Glu Val Cys Val Ala Val Trp Arg Lys
            260                 265                 270
Asn Asp Lys Asn Ile Thr Leu Glu Thr Val Cys His Asp Pro Lys Leu
            275                 280                 285
Thr Tyr His Gly Phe Thr Leu Glu Asp Ala Ala Ser Pro Lys Cys Val
290                 295                 300
Met Lys Glu Lys Lys Arg Ala Gly Glu Thr Phe Phe Met Cys Ala Cys
305                 310                 315                 320
Asn Met Glu Glu Cys Asn Asp Tyr Ile Ile Phe Ser Glu Glu Tyr Thr
                325                 330                 335
Thr Ser Ser Pro Asp Leu Leu Leu Val Ile Ile Gln Val Thr Asp Pro
            340                 345                 350
Leu
```

<210> SEQ ID NO 3
<211> LENGTH: 985
<212> TYPE: DNA
<213> ORGANISM: Artificial Sequence
<220> FEATURE:
<223> OTHER INFORMATION: DNA sequence of human IL-2/sT(beta)RIIB

<400> SEQUENCE: 3
atgtacagga tgcaactcct gtcttgcatt gcactaagtc ttgcacttgt cacaaacagt    60

-continued

```
gcacctactt caagttctac aaagaaaaca cagctacaac tggagcattt acttctggat    120
ttacagatga tttttgaatgg aattaataat tacaagaatc ccaaactcac caggatgctc   180
acatttaagt tttacatgcc caagaaggcc acagaactga acatcttca gtgtctagaa     240 gaagaactca aacctctgga ggaagtgcta aatttagctc aaagcaaaaa ctttcactta    300
agacccaggg acttaatcag caatatcaac gtaatagttc tggaactaaa gggatctgaa    360
acaacattca tgtgtgaata tgctgatgag acagcaacca ttgtagaatt tctgaacaga    420
tggatcctca ggggcctgtg gccgctgcac atcgtcctgt ggacgcgtat cgccagcacg    480
atcccaccgc acgttcagaa gtcggatgtg gaaatggagg cccagaaaga tgaaatcatc    540
tgccccagct gtaataggac tgcccatcca ctgagacata ttaataacga catgatagtc    600
actgacaaca acggtgcagt caagtttcca caactgtgta aattttgtga tgtgagattt    660
tccacctgtg acaaccagaa atcctgcatg agcaactgca gcatcacctc catctgtgag    720
aagccacagg aagtctgtgt ggctgtatgg agaaagaatg acgagaacat aacactagag    780
acagtttgcc atgaccccaa gctcccctac catgacttta ttctggaaga tgctgcttct    840
ccaaagtgca ttatgaagga aaaaaaaaag cctggtgaga ctttcttcat gtgttccctgt   900 agctctgatg agtgcaatga caacatcatc ttctcagaag aatataacac cagcaatcct    960
gactgggagc cagtccagga gtgag                                          985
```

<210> SEQ ID NO 4
<211> LENGTH: 328
<212> TYPE: PRT
<213> ORGANISM: Artificial Sequence
<220> FEATURE:
<223> OTHER INFORMATION: Amino-acid sequence of human IL-2/sT(beta)RIIB
      fusion protein

<400> SEQUENCE: 4

```
Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Leu Arg
    130                 135                 140

Gly Leu Trp Pro Leu His Ile Val Leu Trp Thr Arg Ile Ala Ser Thr
145                 150                 155                 160

Ile Pro Pro His Val Gln Lys Ser Asp Val Glu Met Glu Ala Gln Lys
                165                 170                 175

Asp Glu Ile Ile Cys Pro Ser Cys Asn Arg Thr Ala His Pro Leu Arg
            180                 185                 190

His Ile Asn Asn Asp Met Ile Val Thr Asp Asn Asn Gly Ala Val Lys
```

```
                195                 200                 205
Phe Pro Gln Leu Cys Lys Phe Cys Asp Val Arg Phe Ser Thr Cys Asp
210                 215                 220

Asn Gln Lys Ser Cys Met Ser Asn Cys Ser Ile Thr Ser Ile Cys Glu
225                 230                 235                 240

Lys Pro Gln Glu Val Cys Val Ala Val Trp Arg Lys Asn Asp Glu Asn
                245                 250                 255

Ile Thr Leu Glu Thr Val Cys His Asp Pro Lys Leu Pro Tyr His Asp
                260                 265                 270

Phe Ile Leu Glu Asp Ala Ala Ser Pro Lys Cys Ile Met Lys Glu Lys
                275                 280                 285

Lys Lys Pro Gly Glu Thr Phe Phe Met Cys Ser Cys Ser Ser Asp Glu
290                 295                 300

Cys Asn Asp Asn Ile Ile Phe Ser Glu Glu Tyr Asn Thr Ser Asn Pro
305                 310                 315                 320

Asp Phe Trp Glu Pro Val Gln Glu
                325
```

```
<210> SEQ ID NO 5
<211> LENGTH: 1028
<212> TYPE: DNA
<213> ORGANISM: Artificial Sequence
<220> FEATURE:
<223> OTHER INFORMATION: Verified DNA Sequence of mouse IL2/sT(beta)RII
      fusion protein

<400> SEQUENCE: 5
atgtacagca tgcagctcgc atcctgtgtc acattgacac ttgtgctcct tgtcaacagc      60
gcacccactt caagctccac ttcaagctct acagcggaag cacagcagca gcagcagcag    120
cagcagcagc agcagcagca cctggagcag ctgttgatgg acctacagga gctcctgagc    180
aggatggaga attacaggaa cctgaaactc cccaggatgc tcaccttcaa atttacttg     240
cccaagcagg ccacagaatt gaaagatctt cagtgcctag aagatgaact tggacctctg    300
cggcatgttc tggatttgac tcaaagcaaa agctttcaat ggaagatgc tgagaatttc     360
atcagcaata tcagagtaac tgttgtaaaa ctaaagggct ctgacaacac atttgagtgc    420
caattcgatg atgagtcagc aactgtggtg gactttctga ggagatggat agccttctgt    480
caaagcatca tctcaacagc tagcacgatc ccgccgcacg ttcccaagtc ggatgtggaa    540
atggaagccc agaaagatgc atccatccac ctaagctgta taggaccat ccatccactg     600
aaacatttta acagtgatgt catggccagc gacaatggcg gtgcggtcaa gcttccacag    660
ctgtgcaagt tttgcgatgt gagactgtcc acttgcgaca accagaagtc ctgcatgagc    720
aactgcagca tcacggccat ctgtgagaag ccgcatgaag tctgcgtggc cgtgtggagg    780
aagaacgaca gaacattac tctggagacg gtttgccacg accccaagct cacctaccac    840
ggcttcactc tggaagatgc cgcttctccc aagtgtgtca tgaaggaaaa gaaaagggcg    900
ggcgagactt tcttcatgtg tgcctgtaac atggaagagt gcaacgatta tcatcatttt     960
tcggaagaat acaccaccag cagtcccgac ctgttgttgg tcattatcca agtgacggat   1020
ccccctttg                                                           1028
```

```
<210> SEQ ID NO 6
<211> LENGTH: 342
<212> TYPE: PRT
<213> ORGANISM: Artificial Sequence
<220> FEATURE:
<223> OTHER INFORMATION: Verified Amino-acid sequence of mouse
```

IL-2/sT(beta)RII fusion protein

<400> SEQUENCE: 6

Met Tyr Ser Met Gln Leu Ala Ser Cys Val Thr Leu Thr Leu Val Leu
1               5                   10                  15

Leu Val Asn Ser Ala Pro Thr Ser Ser Ser Thr Ser Ser Ser Thr Ala
            20                  25                  30

Glu Ala Gln Gln Gln Gln Gln Gln Gln Gln Gln Gln Gln Gln His Leu
        35                  40                  45

Glu Gln Leu Leu Met Asp Leu Gln Glu Leu Leu Ser Arg Met Glu Asn
    50                  55                  60

Tyr Arg Asn Leu Lys Leu Pro Arg Met Leu Thr Phe Lys Phe Tyr Leu
65                  70                  75                  80

Pro Lys Gln Ala Thr Glu Leu Lys Asp Leu Gln Cys Leu Glu Asp Glu
                85                  90                  95

Leu Gly Pro Leu Arg His Val Leu Asp Leu Thr Gln Ser Lys Ser Phe
            100                 105                 110

Gln Leu Glu Asp Ala Glu Asn Phe Ile Ser Asn Ile Arg Val Thr Val
        115                 120                 125

Val Lys Leu Lys Gly Ser Asp Asn Thr Phe Glu Cys Gln Phe Asp Asp
    130                 135                 140

Glu Ser Ala Thr Val Val Asp Phe Leu Arg Arg Trp Ile Ala Phe Cys
145                 150                 155                 160

Gln Ser Ile Ile Ser Thr Ala Ser Thr Ile Pro Pro His Val Pro Lys
                165                 170                 175

Ser Asp Val Glu Met Glu Ala Gln Lys Asp Ala Ser Ile His Leu Ser
            180                 185                 190

Cys Asn Arg Thr Ile His Pro Leu Lys His Phe Asn Ser Asp Val Met
        195                 200                 205

Ala Ser Asp Asn Gly Gly Ala Val Lys Leu Pro Gln Leu Cys Lys Phe
    210                 215                 220

Cys Asp Val Arg Leu Ser Thr Cys Asp Asn Gln Lys Ser Cys Met Ser
225                 230                 235                 240

Asn Cys Ser Ile Thr Ala Ile Cys Glu Lys Pro His Glu Val Cys Val
                245                 250                 255

Ala Val Trp Arg Lys Asn Asp Lys Asn Ile Thr Leu Glu Thr Val Cys
            260                 265                 270

His Asp Pro Lys Leu Thr Tyr His Gly Phe Thr Leu Glu Asp Ala Ala
        275                 280                 285

Ser Pro Lys Cys Val Met Lys Glu Lys Lys Arg Ala Gly Glu Thr Phe
    290                 295                 300

Phe Met Cys Ala Cys Asn Met Glu Glu Cys Asn Asp Tyr Ile Ile Phe
305                 310                 315                 320

Ser Glu Glu Tyr Thr Thr Ser Ser Pro Asp Leu Leu Leu Val Ile Ile
                325                 330                 335

Gln Val Thr Asp Pro Leu
            340

<210> SEQ ID NO 7
<211> LENGTH: 948
<212> TYPE: DNA
<213> ORGANISM: Artificial Sequence
<220> FEATURE:
<223> OTHER INFORMATION: DNA sequence of modified human IL-2/sT(beta)RIIB

<400> SEQUENCE: 7

```
atgtacagga tgcaactcct gtcttgcatt gcactaagtc ttgcacttgt cacaaacagt    60
gcacctactt caagttctac aaagaaaaca cagctacaac tggagcattt acttctggat   120
ttacagatga ttttgaatgg aattaataat tacaagaatc ccaaactcac caggatgctc   180
acatttaagt tttacatgcc caagaaggcc acagaactga acatcttca gtgtctagaa    240 gaagaactca aacctctgga ggaagtgcta aatttagctc aaagcaaaaa ctttcactta   300
agacccaggg acttaatcag caatatcaac gtaatagttc tggaactaaa gggatctgaa   360
acaacattca tgtgtgaata tgctgatgag acagcaacca ttgtagaatt tctgaacaga   420
tggatccgta tcgccagcac gatcccaccg cacgttcaga agtcggatgt ggaaatggag   480
gcccagaaag atgaaatcat ctgccccagc tgtaatagga ctgcccatcc actgagacat   540
attaataacg acatgatagt cactgacaac aacggtgcag tcaagtttcc acaactgtgt   600
aaattttgtg atgtgagatt ttccacctgt gacaaccaga atcctgcat gagcaactgc    660 agcatcacct ccatctgtga agccacag gaagtctgtg tggctgtatg agaaagaat      720 gacgagaaca taacactaga gacagtttgc catgacccca agctccccta ccatgacttt   780
attctggaag atgctgcttc tccaaagtgc attatgaagg aaaaaaaaa gcctggtgag    840 actttcttca tgtgttcctg tagctctgat gagtgcaatg acaacatcat cttctcagaa   900
gaatataaca ccagcaatcc tgaattctgg gagccagtcc aggagtga              948
```

<210> SEQ ID NO 8
<211> LENGTH: 315
<212> TYPE: PRT
<213> ORGANISM: Artificial Sequence
<220> FEATURE:
<223> OTHER INFORMATION: Amino acid sequence of modified human
IL-2/sT(beta)RIIB

<400> SEQUENCE: 8

```
Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Arg Ile
    130                 135                 140

Ala Ser Thr Ile Pro Pro His Val Gln Lys Ser Asp Val Glu Met Glu
145                 150                 155                 160

Ala Gln Lys Asp Glu Ile Ile Cys Pro Ser Cys Asn Arg Thr Ala His
                165                 170                 175

Pro Leu Arg His Ile Asn Asn Asp Met Ile Val Thr Asp Asn Asn Gly
            180                 185                 190
```

-continued

```
Ala Val Lys Phe Pro Gln Leu Cys Lys Phe Cys Asp Val Arg Phe Ser
        195                 200                 205

Thr Cys Asp Asn Gln Lys Ser Cys Met Ser Asn Cys Ser Ile Thr Ser
    210                 215                 220

Ile Cys Glu Lys Pro Gln Glu Val Cys Val Ala Val Trp Arg Lys Asn
225                 230                 235                 240

Asp Glu Asn Ile Thr Leu Glu Thr Val Cys His Asp Pro Lys Leu Pro
                245                 250                 255

Tyr His Asp Phe Ile Leu Glu Asp Ala Ala Ser Pro Lys Cys Ile Met
            260                 265                 270

Lys Glu Lys Lys Lys Pro Gly Glu Thr Phe Phe Met Cys Ser Cys Ser
        275                 280                 285

Ser Asp Glu Cys Asn Asp Asn Ile Ile Phe Ser Glu Glu Tyr Asn Thr
    290                 295                 300

Ser Asn Pro Glu Phe Trp Glu Pro Val Gln Glu
305                 310                 315
```

INTERLEUKIN-2/SOLUBLE TGA-BETA TYPE II RECEPTOR B CONJUGATES AND METHODS AND USES THEREOF

CROSS REFERENCE TO RELATED APPLICATIONS

This is a continuation-in-part of PCT/CA2009/000841 filed on Jun. 19, 2009, which claims priority from U.S. provisional application 61/074,369 filed on Jun. 20, 2008, both of which are incorporated herein by reference in their entirety.

INCORPORATION OF SEQUENCE LISTING

A computer readable form of the Sequence Listing "17486NP_SequenceListing.txt" (17,739 bytes), submitted via EFS-WEB and created on Dec. 20, 2010, is herein incorporated by reference.

FIELD OF THE DISCLOSURE

The disclosure relates to conjugates useful in cancer immunotherapy. In particular, the disclosure relates to the conjugate of IL-2, with the alternatively spliced isoform of the soluble form of the TGF-beta receptor type II B (TβRIIB) and methods and uses thereof.

BACKGROUND OF THE DISCLOSURE

The members of the Transforming Growth Factor beta (TGFβ) family are cytokines involved in essential cellular functions such as proliferation, differentiation, apoptosis, tissue remodeling, angiogenesis, immune response, cell adhesion, and also play a key role in pathophysiology of disease states as different as chronic inflammatory conditions and cancer. TGFβ initiates signaling by binding and bringing together type II (TβRII) and type I (TβRI) receptor serine/threonine kinases on the cell surface. TβRII phosphorylates the TβRI, which in turn phosphorylates receptor regulated SMADs (R-SMADs), i.e., SMAD2 and SMAD3. Activated SMADs heterodimerize with a common-partner SMAD4. Subsequently, the heterodimers, i.e., SMAD2/SMAD4 and SMAD3/SMAD4 translocate into the nucleus, where they cooperate with other transcription factors to modulate the expression of TGFβ target genes.

A negative feedback mechanism mediated by inhibitory Smads such as Smad6 and Smad7 acts to inactivate TGFβ signalling pathways by preventing the interaction of the TGFβ receptor complex with Smad2 and Smad3 (Ulloa et al. 1999; Kaysak et al. 2000; Massague et al. 2005). Moreover, the inhibitory Smad7 may recruit phosphatases and ubiquitin ligases to the activated TGFβ receptors and thereby inactivate said receptors by promoting their dephosphorylation and degradation.

Most cell types express three types of receptors for TGF-β. These are designated Type I (53 kDa), Type II (70-85 kDa) and type III (250-350 kDa). The Type III receptor, a proteoglycan that exists in membrane-bound and soluble forms, binds TGF-β1, TGF-β2 and TGF-β3 but does not appear to be involved in signal transduction. The Type II receptor is a membrane-bound serine/threonine kinase that binds TGF-β1 and TGF-β3 with high affinity and TGF-β2 with a much lower affinity. The Type I receptor is also a membrane-bound serine/threonine kinase that apparently requires the presence of the Type II receptor to bind TGF-β. Current evidence suggests that signal transduction requires the cytpolasmic domains of both the Type I and Type II receptors. A short form of TβRII has been described by the Whitehead Institute for Medical Research (WO9309228).

An alternatively spliced form of the Type II Receptor, referred to as TβRIIB, was described for mouse and human (Suzuki et al.,1995; Ogasa et al., 1996) and comprises an additional 75 bp coding for 25 amino acids. Thus, the alternative splicing results in an insertion of 26 amino acids in exchange for Val32 in the mouse and human extracellular domain of the receptor. This structural alteration leads to a new binding site for TGF-β2 without abolishing binding to the other isoforms, TGF-β1 and -β3. Both TβRII and TβRIIB bind TGF-β1 and TGF-β3 with high affinity. However, only TβRIIB also binds TGF-β2 with high affinity in the absence of TβRIII.

While TβRII is ubiquitously expressed, the splicing variant TβRIIB shows a restricted expression pattern in osteoblasts, mesenchymal precursor cells with upregulated levels during their differentiation into myoblasts, and in the heart. In the absence of TBRIII, TβRIIB binds to TGF-β2 and signals without the requirement of TβRIII. TβRIIB heterodimerizes with the wild-type or short form TβRII and binds all the three ligands TGF-β1, TGF-β2 and TGF-β3 (Krishnaveni et al., 2006). TβRIIB may play an important role in TGF-β2 binding and signaling in cells lacking TβRIII (Nikawa 1994; Rotzer, D. et al., 2001). In mammals the three TGF betas TGF-β1, TGF-β2, and TGF-β3 often show overlapping functions despite the fact that isoform specific knock-out mice revealed non-redundant and non-overlapping phenotypes.

Expression of the variant TβRIIB was found in all prostate cell lines studied with a preferential localization in epithelial cells in some human prostatic glands (Konrad et al., 2007). The expression of TβRIIB correlates with the unique expression pattern of TGF-β2 in chondrocytes and osteocytes (Rotzer et al., 2001). TGF-β2 is the only ligand that has a demonstrated role in epithelial mesenchymal cell transformation (EMT), a process defined by the loss of epithelial characteristics and the acquisition of a mesenchymal phenotype. In carcinoma cells, EMT can be associated with increased aggressiveness, and invasive and metastatic potential.

Previously performed research by Del Re et al. (2004) showed that the soluble extracellular domain of the TβRII, consisting of the extracellular domain of the receptor and the Fc part of a human immunoglobulin, bound TGF-β1 and TGF-β3 with high affinity but did not bind TGF-β2 in the same dose range.

While TGFβ has been considered a tumor suppressor factor because it promotes cell growth inhibition, apoptosis and differentiation (Gorelik and Flavell 2002), an extensive number of studies attest to the fact that TGFβ acts as a potent tumor promoter in established breast carcinoma, melanoma, gliomas among others.

In late stage tumor, breast cancer cells synthesize and secrete high levels of active TGFβ protein that can be found in both tumor cells and in plasma of breast cancer patients, both of which are associated with poor prognosis (Gorelik and Flavell 2002). As tumors progress, tumor-derived TGFβ becomes oncogenic by constitutively inducing epithelial to mesenchymal transition (EMT) and tumor associated angiogenesis and by suppressing tumor specific immunity, which combined promotes tumor growth and metastasis. As a prometastatic factor, TGFβ induces both the degradation of extracellular matrix and epithelial-to-mesenchymal transition of normal and transformed epithelial cells and thus enhanced migratory ability. In addition, TGFβ promotes myofibroblast differentiation and angiogenesis. Tumor derived-TGFβ also suppresses antitumor immune response by directly inhibiting the activation of cytolytic T cells, NK cells and macrophages, as well as interfering with dendritic cell function.

Consistent with this notion, several therapeutic approaches target TGFβ pathways for the treatment of invasive cancers such as breast cancer and melanoma. For instance, intracellular inhibition of TGFβ receptor I (TβRI) kinase with small-molecule inhibitors (Ki26894, SD-093 and SB-203580), effectively reduces number and size of lung metastases in both orthotropic xenografts and experimental metastasis models of breast carcinoma (Ge et al. 2006). Other small compounds (SD-093 and LY580276), inhibitors of epithelial-to-mesenchymal transition, also suppress tumor cell invasion and metastasis (Peng et al. 2005). In addition, antagonists of TGFβ binding to heteromeric receptor, such as a soluble Fc:TGFβ type II receptor fusion protein (Fc:TβRII), have shown significant reduction of tumor cell motility, intravasation, and lung metastases in three experimental models of breast cancer. However, this treatment strategy did not alter cellular proliferation (Muraoka et al. 2002), which indicates that the antimetastatic effect of Fc:TβRII in vivo was independent of tumor cell proliferation. Similar results were obtained with a monoclonal anti-TGFβ antibody (1D11), which also suppresses metastasis in highly metastatic model of breast cancer (4T1 cells), without significantly affecting tumor cell proliferation (Nam et al. 2006). Not only does TGFβ act as a prometastatic factor in advanced breast cancer, but it also exerts severe deleterious effects on several components of the immune response against cancer cells, abolishing the effector functions of macrophages, cytotoxic T cells, dendritic cells and NK cells, where TGFβ acts as a negative regulator of IFNγ production via its mediators SMAD2, SMAD3 and SMAD4. WO9804802 and US20050203022 disclose a fusion of the extracellular ectodomain of TβRII with the IgG immunoglobulin heavy chain. This molecule acts as a decoy trap for TGFβ.

Proinflammatory cytokines such as IL-2 constitute useful adjuvants for which extensive clinical experience exists for treatment of cancer. Cytokines can be used independently and combined as part of a fusokine to generate whole cell tumor vaccines as previously published (Stagg et al. 2004). Indeed, IL-2 is able to promote an innate antitumor response by inducing loco-regional tumor rejection, acting as an autocrine factor for T cells and supporting the development of cytotoxic T cells, and by stimulating NK cell proliferation and cytolytic activity. Despite the potent proinflammatory response initiated by cytokines, it has been recently discovered that tumor-derived TGFβ acts as a powerful and overwhelming dominant negative effect on the immune system, especially when a large tumor burden exists (Penafuerte and Galipeau 2008).

SUMMARY OF THE DISCLOSURE

The present inventors have shown that combining the proinflammatory cytokine interleukin-2 (IL-2) with the alternatively spliced TGF-beta Type II Receptor (TβRIIB) ectodomain promotes proliferation and differentiation of antigen-presenting cells and immune effector cells, which initiates a tumor-specific immune response that can be subsequently amplified by sequestration and neutralization of tumor-derived TGFβ. The resulting fusokine is also referred to herein as FIST.

Accordingly, in one aspect, the present disclosure provides a conjugate protein comprising an IL-2 or a fragment thereof linked to a sTβRIIB or a fragment thereof. In one embodiment, the IL-2 or fragment thereof is linked to the sTβRIIB or fragment thereof by a peptide linker. In another embodiment, the linker has 1 to 15 amino acids. In a further embodiment, the conjugate protein has the amino acid sequence shown in SEQ ID NO:2 or 4 or a homolog or analog thereof. In yet another embodiment, the conjugate protein has the amino acid sequence shown in SEQ ID NO:6 or 8.

In another aspect, the present disclosure provides a nucleic acid molecule comprising a nucleic acid sequence encoding the conjugate protein described herein. In one embodiment, the nucleic acid molecule encoding the conjugate protein has the nucleotide sequence shown in SEQ ID NO:1 or 3 or a homolog or analog thereof. In another embodiment, the nucleic acid molecule encoding the conjugate protein has the nucleotide sequence shown in SEQ ID NO:5 or 7 or a homolog or analog thereof. In a further embodiment, the disclosure provides an expression vector comprising the nucleic acid operably linked to an expression control sequence. In yet another embodiment, the present disclosure provides a cell comprising the expression vector or progeny of said cell wherein said cell expresses the conjugate protein.

In a further aspect, the disclosure provides a method of treating cancer comprising administering an effective amount of a conjugate protein comprising an IL-2 or a fragment thereof linked to a sTβRIIB or a fragment thereof or a nucleic acid encoding the conjugate protein to an animal or cell in need thereof. The disclosure also provides a use of an effective amount of a conjugate protein comprising an IL-2 or a fragment thereof linked to a sTβRIIB or a fragment thereof or a nucleic acid encoding the conjugate protein for treating cancer. The disclosure further includes a use of an effective amount of a conjugate protein comprising an IL-2 or a fragment thereof linked to a sTβRIIB or a fragment thereof or a nucleic acid encoding the conjugate protein in the preparation of a medicament for treating cancer. The disclosure also provides an effective amount of a conjugate protein comprising an IL-2 or a fragment thereof linked to a sTβRIIB or a fragment thereof or a nucleic acid encoding the conjugate protein for use in treating cancer. In an embodiment, the cancer is any cancer that produces TGF-beta. In another embodiment, the cancer is an adenocarcinoma, such as, lung, breast, bowel, prostate or lymphomas. In one embodiment, the cancer is breast cancer, melanoma or glioma. In another embodiment, the method treats the primary tumour. In yet another embodiment, the method treats metastatic or secondary tumour.

In a further aspect, the disclosure provides a pharmaceutical composition comprising an effective amount of a conjugate protein comprising an IL-2 or a fragment thereof linked to a sTβRIIB or a fragment thereof or a nucleic acid molecule encoding the conjugate protein in admixture with a suitable diluent or carrier.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

The disclosure will now be described in relation to the drawings in which:

FIG. 1 shows the sequence (A) (SEQ ID NO:2) of the murine fusion protein IL-2/sTβRIIB (mFIST) and its characterization by Western Blot (B) and Immunoprecipitation (C).

FIG. 8 shows the suppression of angiogenesis by mFIST and human FIST (hFIST) compared to soluble TGFβ RIIB, IL-2 and their combination depicted as matrigel graph and final score.

FIG. 10 shows the characterization of ex vivo mFIST stimulated B cells as potent antigen presenting cells (APC) in vitro (A) and in vivo (B). mFIST stimulated B cells induced T cells to produce IFN-γ and IL-2 in an antigen dependent manner (A) and suppressed tumor development in mice injected with EG7 tumor cells and led to 100% survival and tumor free mice until at least 50 days after implantation.

FIG. 11 shows the sequence (A) (SEQ ID NO:4) of the human fusion protein IL-2/sTβRIIB (hFIST) and its detection by Western Blot (B), characterization by proliferation assay (C) and the stimulation of IFN-γ production in human peripheral blood cells (D).

FIG. 12 shows a comparison of the yield of human fusokine having the sequence as shown in SEQ ID NO:4 with the human fusokine having the sequence as shown in SEQ ID NO:8.

DETAILED DESCRIPTION OF THE DISCLOSURE

Figure 2:
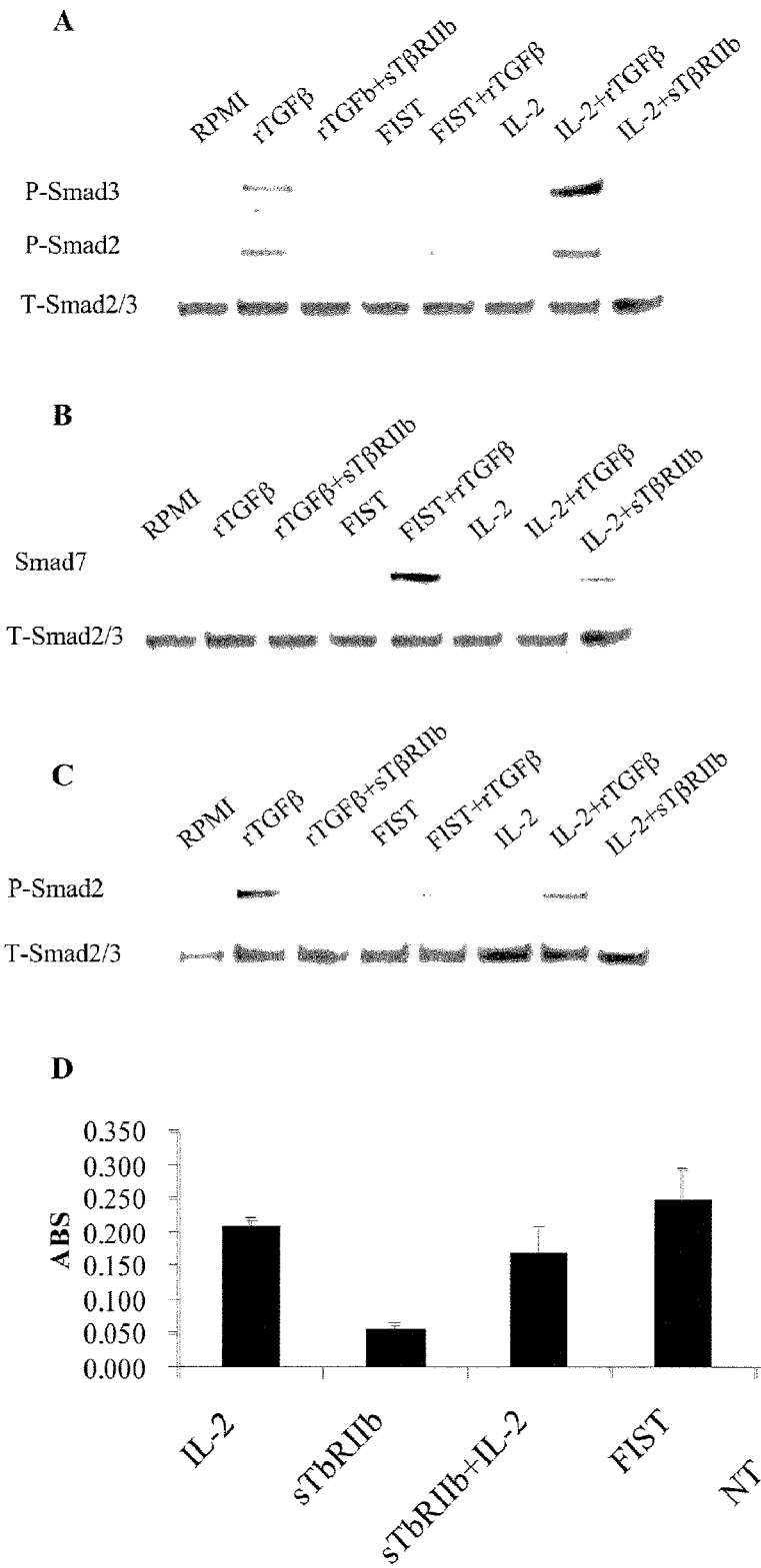
FIG. 2 shows the activation profiles of Smad 2, 3 (A, C) and Smad 7 expression (B) and proliferation (D) induced by mFIST compared to soluble TGFβ RIIB, IL-2 and their combinations. Results in C were generated in human NK92 cells whereas A,B, and D were generated in mouse cells.

The present inventors have shown a successfully generated chimeric protein consisting of the fusion of IL-2 and the ectodomain of TGFβ receptor type IIB (TβRIIB) (hereafter: IL-2/sTβRIIB or FIST). In vitro data demonstrate that IL-2/sTβRIIB have a dominant negative effect on TGFβ related signalling pathways by inhibiting the phosphorylation of Smad2 and Smad3. IL-2/sTβRIIB also induces de novo expression of Smad7. As an immunostimulator, the IL-2/sTβRIIB primes splenocytes to produce a twenty fold greater amount of IFNγ than equimolar concentrations of IL-2. In contrast with IL-2, this effect was not suppressed in the presence of TGFβ. Without wishing to be bound by any theory, the present inventors have observed a robust activation of the JAK/STAT pathway with IL-2/sTβRIIB.

A. Proinflammatory-2 and Soluble TGF-Beta Transforming Growth Factor Type II Receptor Conjugate The present disclosure relates to conjugates of IL-2 and sTβRIIB that can be used for treating cancer, stimulating the immune response and/or inhibiting angiogenesis as described in Section B.

Accordingly, the present disclosure provides a conjugate protein comprising an IL-2 or a fragment thereof linked to a sTβRIIB or a fragment thereof.

The term "interleukin-2 or IL-2" as used herein refers to IL-2 from any species or source and includes the full-length protein as well as fragments or portions of the protein. Mouse IL-2 has the Genbank accession number AAD25890 and human IL-2 has the Genbank accession number AAG53575. The term "IL-2 fragment" as used herein means a portion of the IL-2 peptide that contains at least 10%, 20%, 30%, 40%, 50%, 60%, 70%, 80%, 90%, 95%, or more of the entire length of the IL-2 polypeptide. In one embodiment, the IL-2 is truncated at the N-terminal or C-terminal end to permit cloning.

The term "soluble transforming growth factor (TGF)-beta receptor type II B or sTβRIIB" as used herein refers to a soluble, or non-membrane form of the alternatively spliced transforming growth factor beta type II receptor, preferably the ectodomain of the TGF-beta type II receptor from any species or source and includes the full-length ectodomain as well as fragments or portions of the ectodomain. In a preferred embodiment, the sTβRIIB is human or mouse. The mouse TGF-beta receptor II has the Genbank accession number Q62312, and in one embodiment, the soluble form contains the sequence from Arg19 to Thr193. The human TGF-beta receptor II has the Genbank accession number ABG65632, and in one embodiment, the soluble form contains the sequence from Leu9 to Asp 184. The term "sTβRIIB fragment" as used herein means at least 10%, 20%, 30%, 40%, 50%, 60%, 70%, 80%, 90%, 95%, or more of the entire length of the reference polypeptide. In one embodiment, the IL-2 is truncated at the N-terminal or C-terminal end to permit cloning.

The term "conjugate protein" as used herein means a conjugate that comprises an IL-2 or a fragment thereof physically linked to a sTβRIIB or a fragment thereof. In a specific embodiment, the conjugate is a fusion protein (or fusokine) wherein a nucleic acid sequence encoding the IL-2 or fragment thereof is operably linked to a nucleic acid sequence encoding the sTβRIIB and the chimeric sequence is transfected or transduced into a host cell and produced as a recombinant fusion protein.

In an embodiment, the IL-2 or fragment thereof and sTβRIIB are linked by a peptide linker. The peptide linker can be any size provided it does not interfere with the function of the conjugate protein. In one embodiment, the peptide linker is from about 1 to about 15 amino acids in length, more specifically from about 1 to about 10 amino acids, and most specifically from about 1 to about 6 amino acids.

One of skill in the art can appreciate that the conjugate protein can also be formed by linking the two proteins in vitro, for example, using chemical cross-linkers. For example, the proteins may be coupled using heterobifunctional thiol-containing linkers as described in WO 90/10457, N-succinimidyl-3-(2-pyridyldithio-proprionate) or N-succinimidyl-5 thioacetate.

In one embodiment, the conjugate protein is murine and has the amino acid sequence shown in SEQ ID NO:2 or 6 or an analog or homolog thereof. In another embodiment, the conjugate protein is human and has the amino acid sequence shown in SEQ ID NO:4 or 8 or an analog or homolog thereof. This IL-2 and sTβRIIB conjugate protein is abbreviated IL-2/sTβRIIB and also called "FIST". The conjugate protein derived from murine sequences is abbreviated mFIST and the conjugate protein derived from human sequences is abbreviated hFIST.

The disclosure also includes nucleic acid molecules that encode the conjugate proteins described herein. The nucleic acid molecule is preferably a chimeric nucleic acid sequence that comprises a) a nucleic acid sequence encoding the IL-2 or fragment thereof linked to b) a nucleic acid sequence encoding sTβRIIB or a fragment thereof.

The chimeric sequence optionally also includes a sequence encoding a peptide linker. Accordingly, the present disclosure also includes a chimeric nucleic acid sequence that comprises a) a nucleic acid sequence encoding the IL-2 or fragment thereof linked to b) a nucleic acid sequence encoding a peptide linker linked to c) a nucleic acid sequence encoding the sTβRIIB or fragment thereof.

In one embodiment, the chimeric nucleic acid sequence is murine and has the nucleotide sequence shown in SEQ ID NO:1 or 5, or a homolog or analog thereof. In another embodiment, the chimeric nucleic acid sequence is human and has the nucleotide sequence shown in SEQ ID NO:3 or 7, or a homolog or analog thereof. The nucleic acid encoding the conjugate protein is abbreviated IL-2/sTβRIIB.

The term "homolog" means those amino acid or nucleic acid sequences which have slight or inconsequential sequence variations from the sequences in SEQ ID NOs:1-8, i.e., the sequences function in substantially the same manner. The variations may be attributable to local mutations or structural modifications. Sequences having substantial homology include nucleic acid sequences having at least 65%, more preferably at least 85%, and most preferably 90-95% identity with the sequences as shown in SEQ ID NOs:1-8. Sequence identity can be calculated according to methods known in the art. Nucleic acid sequence identity is most preferably assessed by the algorithm of BLAST version 2.1 advanced search. BLAST is a series of programs that are available online (see world wide web at ncbi.nlm.nih.gov/BLAST). The advanced blast search (see world wide web at ncbi.nlm.nih.gov/ blast/blast.cgi?Jform=1) is set to default parameters. (ie Matrix BLOSUM62; Gap existence cost 11; Per residue gap cost 1; Lambda ratio 0.85 default). References to BLAST searches are: Altschul, S. F., Gish, W., Miller, W., Myers, E. W. & Lipman, D. J. (1990) "Basic local alignment search tool." J. Mol. Biol. 215:403410; Gish, W. & States, D. J. (1993) "Identification of protein coding regions by database similarity search." Nature Genet. 3:266272; Madden, T. L., Tatusov, R. L. & Zhang, J. (1996) "Applications of network BLAST server" Meth. Enzymol. 266:131_141; Altschul, S.F., Madden, T.L., Schäffer, A.A., Zhang, J., Zhang, Z., Miller, W. & Lipman, D. J. (1997) "Gapped BLAST and PSI_BLAST: a new generation of protein database search programs." Nucleic Acids Res. 25:33893402; Zhang, J. & Madden, T. L. (1997) "PowerBLAST: A new network BLAST application for interactive or automated sequence analysis and annotation." Genome Res. 7:649656.

The term "analog" means an amino acid or nucleic acid sequence which has been modified as compared to the sequence of SEQ ID NOs:1-8 wherein the modification does not alter the utility of the sequence (e.g. for treating cancer) as described herein. The modified sequence or analog may have improved properties over the sequences shown in SEQ ID NOs:1-8. One example of a nucleic acid modification to prepare an analog is to replace one of the naturally occurring bases (i.e. adenine, guanine, cytosine or thymidine) of the sequence with a modified base such as xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8 amino guanine, 8-thiol guanine, 8-thiolalkyl guanines, 8-hydroxyl guanine and other 8-substituted guanines, other aza and deaza uracils, thymidines, cytosines, adenines, or guanines, 5-trifluoromethyl uracil and 5-trifluoro cytosine.

Another example of a modification is to include modified phosphorous or oxygen heteroatoms in the phosphate backbone, short chain alkyl or cycloalkyl intersugar linkages or short chain heteroatomic or heterocyclic intersugar linkages in the nucleic acid molecules shown in SEQ ID NO:1, 3, 5 or 7. For example, the nucleic acid sequences may contain phosphorothioates, phosphotriesters, methyl phosphonates, and phosphorodithioates.

A further example of an analog of a nucleic acid molecule of the disclosure is a peptide nucleic acid (PNA) wherein the deoxyribose (or ribose) phosphate backbone in the DNA (or RNA), is replaced with a polyamide backbone which is similar to that found in peptides (P. E. Nielsen, et al Science 1991, 254, 1497). PNA analogs have been shown to be resistant to degradation by enzymes and to have extended lives in vivo and in vitro. PNAs also bind stronger to a complimentary DNA sequence due to the lack of charge repulsion between the PNA strand and the DNA strand. Other nucleic acid analogs may contain nucleotides containing polymer backbones, cyclic backbones, or acyclic backbones. For example, the nucleotides may have morpholino backbone structures (U.S. Pat. No. 5,034,506). The analogs may also contain groups such as reporter groups, a group for improving the pharmacokinetic or pharmacodynamic properties of nucleic acid sequence.

The disclosure also includes sequences that hybridize to the sequences shown in SEQ ID NO:1, 3, 5 or 7 or a fragment thereof and maintain the property of cancer immunotherapy. The term "sequence that hybridizes" means a nucleic acid sequence that can hybridize to a sequence of SEQ ID NO:1, 3, 5 or 7 under stringent hybridization conditions. Appropriate "stringent hybridization conditions" which promote DNA hybridization are known to those skilled in the art, or may be found in Current Protocols in Molecular Biology, John Wiley & Sons, N.Y. (1989), 6.3.1-6.3.6. The term "stringent hybridization conditions" as used herein means that conditions are selected which promote selective hybridization between two complementary nucleic acid molecules in solution. Hybridization may occur to all or a portion of a nucleic acid sequence molecule. The hybridizing portion is at least 50% the length with respect to one of the polynucleotide sequences encoding a polypeptide. In this regard, the stability of a nucleic acid duplex, or hybrids, is determined by the Tm, which in sodium containing buffers is a function of the sodium ion concentration, G/C content of labeled nucleic acid, length of nucleic acid probe (I), and temperature (Tm=81.5° C.−16.6 (Log 10 [Na+])+0.41(%(G+C)−600/I).

Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a greater than 95% identity, the final wash will be reduced by 5° C. Based on these considerations stringent hybridization conditions shall be defined as: hybridization at 5× sodium chloride/sodium citrate (SSC)/5× Denhardt's solution/1.0% SDS at Tm (based on the above equation)−5° C., followed by a wash of 0.2×SSC/0.1% SDS at 60° C.

It will be appreciated that analogs/homologs of the conjugate proteins of the disclosure can also be prepared by first preparing or using an analog or homolog of the IL-2 or sTβRIIB or both prior to preparing the chimeric nucleic acid sequence.

The conjugate proteins of the disclosure may be modified to contain amino acid substitutions, insertions and/or deletions that do not alter the properties of the conjugate protein. Conserved amino acid substitutions involve replacing one or more amino acids of the IL-2 and sTβRIIB conjugate protein with amino acids of similar charge, size, and/or hydrophobicity characteristics. When only conserved substitutions are made the resulting analog should be functionally equivalent to the IL-2 and sTβRIIB conjugate protein. Non-conserved substitutions involve replacing one or more amino acids of the IL-2 and sTβRIIB conjugate protein with one or more amino acids which possess dissimilar charge, size, and/or hydrophobicity characteristics.

The conjugate proteins of the disclosure may be modified to make it more therapeutically effective or suitable. For example, the conjugate protein or peptides of the present disclosure may be converted into pharmaceutical salts by reacting with inorganic acids including hydrochloric acid, sulphuric acid, hydrobromic acid, phosphoric acid, etc., or organic acids including formic acid, acetic acid, propionic acid, glycolic acid, lactic acid, pyruvic acid, oxalic acid, succinic acid, malic acid, tartaric acid, citric acid, benzoic acid, salicylic acid, benzenesulphonic acid, and toluenesulphonic acids.

The disclosure also includes expression vectors comprising a chimeric nucleic acid sequence comprising a) a nucleic acid sequence encoding an IL-2 or a fragment thereof linked to b) a nucleic acid sequence encoding a sTβRIIB or a fragment thereof. In a further embodiment, the chimeric nucleic acid sequence includes a sequence that encodes a peptide linker as described above.

Possible expression vectors include but are not limited to cosmids, plasmids, artificial chromosomes, viral vectors or modified viruses (e.g. replication defective retroviruses, adenoviruses and adeno-associated viruses), so long as the vector is compatible with the host cell used. The expression vectors are "suitable for transformation of a host cell", which means that the expression vectors contain a nucleic acid molecule of the disclosure and regulatory sequences selected on the basis of the host cells to be used for expression, which is operatively linked to the nucleic acid molecule. "Operatively linked" is intended to mean that the nucleic acid is linked to regulatory sequences in a manner which allows expression of the nucleic acid.

The disclosure therefore contemplates a recombinant expression vector of the disclosure containing a nucleic acid molecule of the disclosure, or a fragment thereof, and the necessary regulatory sequences for the transcription and translation of the inserted protein-sequence.

Suitable regulatory sequences may be derived from a variety of sources, including bacterial, fungal, viral, mammalian, or insect genes (for example, see the regulatory sequences described in Goeddel, Gene Expression Technology: Methods in Enzymology 185, Academic Press, San Diego, Calif. (1990). Selection of appropriate regulatory sequences is dependent on the host cell chosen as discussed below, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector. It will also be appreciated that the necessary regulatory sequences may be supplied by the IL-2 or sTβRIIB sequences and/or their flanking regions.

The recombinant expression vectors of the disclosure may also contain a selectable marker gene which facilitates the selection of host cells transformed or transfected with a recombinant molecule of the disclosure. Examples of selectable marker genes are genes encoding a protein such as G418 and hygromycin which confer resistance to certain drugs, β-galactosidase, chloramphenicol acetyltransferase, firefly luciferase, or an immunoglobulin or portion thereof such as the Fc portion of an immunoglobulin preferably IgG. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors of the disclosure and in particular to determine the effect of a mutation on expression and phenotype. It will be appreciated that selectable markers can be introduced on a separate vector from the nucleic acid of interest.

The recombinant expression vectors may also contain genes which encode a moiety which provides increased expression of the recombinant protein; increased solubility of the recombinant protein; and aid in the purification of the target recombinant protein by acting as a ligand in affinity purification. For example, a proteolytic cleavage site may be added to the target recombinant protein to allow separation of the recombinant protein from the fusion moiety subsequent to purification of the fusion protein. Typical fusion expression vectors include pGEX (Amrad Corp., Melbourne, Australia), pMal (New England Biolabs, Beverly, Mass.) and pRIT5 (Pharmacia, Piscataway, N.J.) which fuse glutathione S-transferase (GST), maltose E binding protein, or protein A, respectively, to the recombinant protein.

Recombinant expression vectors can be introduced into host cells to produce a transformed host cell. The term "transformed host cell" is intended to include cells that are capable of being transformed or transfected with a recombinant expression vector of the disclosure. The terms "transduced", "transformed with", "transfected with", "transformation" and "transfection" are intended to encompass introduction of nucleic acid (e.g. a vector or naked RNA or DNA) into a cell by one of many possible techniques known in the art. Prokaryotic cells can be transformed with nucleic acid by, for example, electroporation or calcium-chloride mediated transformation. For example, nucleic acid can be introduced into mammalian cells via conventional techniques such as calcium phosphate or calcium chloride co-precipitation, DEAE-dextran mediated transfection, lipofectin, electroporation, microinjection, RNA transfer, DNA transfer, artificial chromosomes, viral vectors and any emerging gene transfer technologies. Suitable methods for transforming and transfecting host cells can be found in Sambrook et al. (Molecular Cloning: A Laboratory Manual, 2nd Edition, Cold Spring Harbor Laboratory press (1989)), and other laboratory textbooks.

Suitable host cells include a wide variety of eukaryotic host cells and prokaryotic cells. For example, the proteins of the disclosure may be expressed in yeast cells or mammalian cells. Other suitable host cells can be found in Goeddel, Gene Expression Technology: Methods in Enzymology 185, Academic Press, San Diego, Calif. (1991). In addition, the proteins of the disclosure may be expressed in prokaryotic cells, such as *Escherichia coli* (Zhang et al., Science 303(5656): 371-3 (2004)).

Mammalian cells suitable for carrying out the present disclosure include, among others: B16FO cells, 293T cells, Mesenchymal Stromal Cell (MSCs), COS (e.g., ATCC No. CRL 1650 or 1651), BHK (e.g. ATCC No. CRL 6281), CHO (ATCC No. CCL 61), HeLa (e.g., ATCC No. CCL 2), 293 (ATCC No. 1573) and NS-1 cells.

The mammalian cells can also be derived from a human or animal and include stem cells (including hematopoietic stem cells), somatic cells, progenitor cells (including endothelial progenitor cells), fibroblasts, lymphocytes, and mesenchymal stem cells (MSCs) that have been genetically engineered to express the proinflammatory cytokine IL-2 and sTβRIIB conjugate protein. Such cells can be used in the therapeutic applications described in Section B.

Suitable expression vectors for directing expression in mammalian cells generally include a promoter (e.g., derived from viral material such as polyoma, Adenovirus 2, cytomegalovirus and Simian Virus 40), as well as other transcriptional and translational control sequences. Examples of mammalian expression vectors include pCDM8 (Seed, B., Nature 329:840 (1987)), pMT2PC (Kaufman et al., EMBO J. 6:187-195 (1987)) and pCMV (Clontech, California, U.S.A.).

Alternatively, the conjugate proteins of the disclosure may also be expressed in non-human transgenic animals such as, rats, rabbits, sheep and pigs (Hammer et al. Nature 315:680-683 (1985); Palmiter et al. Science 222:809-814 (1983); Brinster et al. Proc. Natl. Acad. Sci. USA 82:4438-4442 (1985); Palmiter and Brinster Cell 41:343-345 (1985) and U.S. Pat. No. 4,736,866). The disclosure also includes tissues and cells derived from such animals.

B. Methods

The conjugate proteins of the disclosure and cells expressing the conjugate proteins have been shown to be effective at stimulating the immune response.

Accordingly, in one aspect, the present disclosure provides a method of stimulating the immune response comprising administering an effective amount of a conjugate protein comprising an IL-2 or a fragment thereof linked to a sTβRIIB or a fragment thereof, or a nucleic acid sequence encoding the conjugate protein to an animal or cell thereof in need of such treatment. The disclosure includes a use of an effective amount of a conjugate protein comprising an IL-2 or a fragment thereof linked to a sTβRIIB or a fragment thereof, or a nucleic acid sequence encoding the conjugate protein for stimulating the immune response. The disclosure includes a use of an effective amount of conjugate protein comprising an IL-2 or a fragment thereof linked to a sTβRIIB or a fragment thereof, or a nucleic acid sequence encoding the conjugate protein to prepare a medicament for stimulating the immune response. In another embodiment, the disclosure provides a conjugate protein comprising an IL-2 or a fragment thereof linked to a sTβRIIB or a fragment thereof, or a nucleic acid sequence encoding the conjugate protein for use in stimulating the immune response. Stimulation of the immune response is useful for treating many diseases, infections and/or cancer. In an embodiment, the conjugate protein stimulates IL-2 Receptor expressing cells, T, B, NK and NKT cells.

The conjugate proteins of the disclosure and cells expressing the conjugate proteins have also been shown to be effective at inhibiting angiogenesis.

Accordingly, in another aspect, the present disclosure provides a method of inhibiting angiogenesis comprising administering an effective amount of a conjugate protein comprising an IL-2 or a fragment thereof linked to a sTβRIIB or a fragment thereof, or a nucleic acid sequence encoding the conjugate protein to an animal or cell thereof in need of such treatment. The disclosure includes a use of an effective amount of a conjugate protein comprising an IL-2 or a fragment thereof linked to a sTβRIIB or a fragment thereof, or a nucleic acid sequence encoding the conjugate protein for inhibiting angiogenesis. The disclosure includes a use of an effective amount of conjugate protein comprising an IL-2 or a fragment thereof linked to a sTβRIIB or a fragment thereof, or a nucleic acid sequence encoding the conjugate protein to prepare a medicament for inhibiting angiogenesis. In another embodiment, the disclosure provides a conjugate protein comprising an IL-2 or a fragment thereof linked to a sTβRIIB or a fragment thereof, or a nucleic acid sequence encoding the conjugate protein for use in inhibiting angiogenesis. Inhibition of angiogenesis is useful for treating cancer, in particular for preventing the growth and/or spread of cancers and is also useful for treating obesity, vascular disorders such as hereditary hemorrhagic telangiectasia (HHT), Marfan syndrome and Loeys-Dietz syndrome, pulmonary arterial hypertension.

The conjugate proteins of the disclosure have been shown to promote an effective antitumor response that blocks tumor metastasis, inhibits tumor growth and prolongs survival. The conjugate proteins of the disclosure can be used for any stage of cancer. For early cancer, the conjugate protein would be useful because the IL-2 can induce a potent anti-cancer immune response that would be subsequently amplified by blocking TGF-beta dependent immunosuppression which commonly occurs as the cancer progresses.

Accordingly, in a further aspect, the present disclosure provides a method of treating cancer comprising administering an effective amount of a conjugate protein comprising an IL-2 or a fragment thereof linked to a sTβRIIB or a fragment thereof, or a nucleic acid sequence encoding the conjugate protein to an animal or cell thereof in need of such treatment. The disclosure includes a use of an effective amount of a conjugate protein comprising an IL-2 or a fragment thereof linked to a sTβRIIB or a fragment thereof, or a nucleic acid sequence encoding the conjugate protein for treating cancer. The disclosure includes a use of an effective amount of conjugate protein comprising an IL-2 or a fragment thereof linked to a sTβRIIB or a fragment thereof, or a nucleic acid sequence encoding the conjugate protein to prepare a medicament to treat cancer. In another embodiment, the disclosure provides a conjugate protein comprising an IL-2 or a fragment thereof linked to a sTβRIIB or a fragment thereof, or a nucleic acid sequence encoding the conjugate protein for use in treating cancer.

In an embodiment, the cancer is any cancer that produces TGF-beta. In another embodiment, the cancer is an adenocarcinoma, such as, lung, breast, bowel, prostate or lymphomas. In yet another embodiment, the cancer is breast cancer, melanoma or glioma. In a further embodiment, the method treats the primary tumour. In another embodiment, the method treats metastatic or secondary tumour.

The term "administering a conjugate protein" includes both the administration of the conjugate protein as well as the administration of a nucleic acid sequence encoding the conjugate protein to an animal or to a cell in vitro (or ex vivo) or in vivo. The term "administering" also includes the administration of a cell that expresses the conjugate protein.

The term "a cell" includes a single cell as well as a plurality or population of cells. Administering to a cell includes administering in vitro (or ex vivo) as well as in vivo.

Administration of an "effective amount" of the conjugate protein and nucleic acid of the present disclosure is defined as an amount effective, at dosages and for periods of time necessary to achieve the desired result. The effective amount of the conjugate protein or nucleic acid of the disclosure may vary according to factors such as the disease state, age, sex, and weight of the animal. Dosage regimens may be adjusted to provide the optimum therapeutic response. For example, several divided doses may be administered daily or the dose may be proportionally reduced as indicated by the exigencies of the therapeutic situation. The mode of administration (e.g. in vivo by injection or ex vivo in culture) will also impact the dosage regime.

The term "animal" as used herein includes all members of the animal kingdom including humans.

Once a particular conjugate protein or analog or homolog is prepared, one of skill in the art can readily determine whether or not it can treat cancer. For example, determining whether a particular conjugate protein or fragment thereof can stimulate an immune response can be assessed using known in vitro immune assays including, but not limited to, proliferation assays, chemotactic assays, cytotoxicity assays, cytokine arrays and determining whether a particular conjugate protein can also bind TGF-beta and thus act as a decoy can be assessed using coimmunoprecipitation.

The term "treatment or treating" as used herein means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treating" can also mean prolonging survival as compared to expected survival if not receiving treatment.

In another embodiment, the methods of the disclosure further comprise combining the treatment with traditional cancer therapies, including chemotherapy, hormonal therapy, surgery, radiotherapy, or Herceptin treatment.

In the above therapeutic applications, the conjugate protein can be administered as a protein or as a nucleic acid molecule encoding the protein. In one embodiment, as noted above, expression of the conjugate protein occurs as a result of the administration of nucleic acid encoding the conjugate protein to an organism. Thus, the conjugate protein will be produced endogenously in the organism, rather than administered in a protein form. The therapy may be done at a later stage of development to specific somatic cells, such that only a particular tissue or portion of a tissue contains the conjugate protein nucleic acid. Techniques for nucleic acid therapy are well known in the art.

It is to be understood that the administration of a conjugate protein nucleic acid in gene therapy may take several forms, all of which are included in the scope of the present disclosure. The nucleic acid encoding the conjugate protein may be administered in such a manner as to add the conjugate protein nucleic acid to the genome of the cell or the organism. For example, administering a nucleic acid encoding the conjugate protein, under the control of a promoter which results in an increased expression of the conjugate protein, results in the incorporation of the nucleic acid into the genome of the cell or the organism, such that increased levels of the conjugate protein are made.

Construction of appropriate expression vehicles and vectors for therapeutic applications will depend on the organism to be treated and the purpose of the gene therapy. The selection of appropriate promoters and other regulatory DNA will proceed according to known principles, based on a variety of known gene therapy techniques. For example, retroviral mediated gene transfer is a very effective method for therapy, as systems utilizing packaging defective viruses allow the production of recombinants which are infectious only once, thus avoiding the introduction of wild-type virus into an organism. Alternative methodologies for therapy include non-viral transfer methods, such as calcium phosphate co-precipitation, mechanical techniques, for example microinjection, membrane fusion-mediated transfer via liposomes, as well as direct DNA uptake and receptor-mediated DNA transfer.

C. Compositions

The disclosure also includes pharmaceutical compositions comprising the conjugate proteins described herein or nucleic acids for use in treating cancer, stimulating the immune response and/or inhibiting angiogenesis.

Such pharmaceutical compositions can be for intralesional, intravenous, topical, rectal, parenteral, local, inhalant or subcutaneous, intradermal, intramuscular, intrathecal, transperitoneal, oral, and intracerebral use. The composition can be in liquid, solid or semisolid form, for example pills, tablets, creams, gelatin capsules, capsules, suppositories, soft gelatin capsules, gels, membranes, tubelets, solutions or suspensions.

The pharmaceutical compositions of the disclosure can be intended for administration to humans or animals or cells or tissue in culture. Dosages to be administered depend on individual needs, on the desired effect and on the chosen route of administration.

The pharmaceutical compositions can be prepared by per se known methods for the preparation of pharmaceutically acceptable compositions which can be administered to patients, and such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 2003—$20^{th}$ Edition) and in The United States Pharmacopeia: The National Formulary (USP 24 NF19) published in 1999.

On this basis, the pharmaceutical compositions include, albeit not exclusively, the active compound or substance in association with one or more pharmaceutically acceptable vehicles or diluents, and contained in buffered solutions with a suitable pH and iso-osmotic with the physiological fluids. The pharmaceutical compositions may additionally contain other anti-cancer agents such as chemotherapeutic drugs, hormonal drugs, and in particular, Herceptin.

In one embodiment, the pharmaceutical composition comprises an effective amount of a conjugate protein comprising an IL-2 or a fragment thereof linked to a sTβRIIB or fragment thereof in admixture with a pharmaceutically acceptable diluent or carrier.

In another embodiment, the pharmaceutical composition comprises an effective amount of a nucleic acid molecule encoding a conjugate protein comprising an IL-2 or a fragment thereof linked to a sTβRIIB or fragment thereof in admixture with a pharmaceutically acceptable diluent or carrier.

The above disclosure generally describes the present disclosure. A more complete understanding can be obtained by reference to the following specific examples. These examples are described solely for the purpose of illustration and are not intended to limit the scope of the disclosure. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1

Results and Discussion:
Design and Characterization of the Murine and the Human IL-2/sTβRII Fusion Protein (aka FIST)

The murine plasmid construct encoding the fusion protein comprises IL-2 and the ectodomain of transforming growth factor β receptor II isoform B (sTBRIIB, from amino acid Arg 19 to Thr 193). The fusokine was created by cloning a modified IL-2 cDNA missing the nucleotides coding for the stop codon in frame with the 5' end of the mouse TβRIIB ectodomain cDNA. The cDNA was sequenced to confirm correct conformation. The final murine fusokine FIST cDNA encodes a single polypeptide chain of 353 amino acids (FIG. 1A). Further verification of the sequence provided the nucleotide sequence as shown in SEQ ID NO:5 and the amino acid sequence as shown in SEQ ID NO:6. The same strategy was used to generate human FIST (IL-2 devoid of stop codon was fused to the long isoform of TGFβ receptor ectodomain (Leu9 to Asp 184)) and results in a 328 amino acid polypeptide (FIG. 11A). These constructs were used to transiently transfect 293T cells. Supernatants from cells transfected with FIST or empty vector were collected after 48 hours, concentrated and probed. The fusion protein was detected by western blot and the protein concentration in the supernatant from transfected 293T cells was quantified by IL-2 ELISA. In addition, co-immunoprecipitation assays were performed using specific antibodies to the extracellular portion of mouse TβRII (FIG. 1B) and TGFβ (FIG. 1C). Both techniques confirmed that the transfected cells secreted the intact fusokine. FIST migrates as an approximately 55 KDa protein in SDS-PAGE under reducing conditions, whereas sTβRIIB ectodomain migrates as a 47 kDa protein (FIG. 1B). The murine FIST precipitated human TGFβ as shown in the FIG. 1C, which indicates that the murine FIST acts as decoy receptor for TGFβ. Similarly, the murine FIST binds to the murine TGFβ in an immunoprecipitation assay in vitro.

FIST Acts as Dominant Negative on TGFβ Signalling Pathway

The balance between proliferative and inhibitory signals is essential to maintain immune homeostasis. In late stage tumor progression, immunostimulatory signals provided by proinflammatory cytokines are antagonized by tumor derived immunosuppressive cytokines, such as TGFβ. Consequently, a prevalent immunosuppression favours tumor growth, invasion and metastasis. The new fusion protein FIST does not only induce the activation of IL-2 receptor and therefore promotes the proliferation of IL-2 dependent cell lines, but also dramatically inhibits the TGFβ signalling pathway by two mechanisms. Firstly, FIST acts as a decoy receptor trap for TGFβ via its TβRIIB ectodomain. Secondly, FIST displays novel immunopharmacologic features regarding the de novo expression of Smad7, an inhibitory Smad that acts as a negative regulator of the TGFβ signalling pathway by preventing the interaction of the TGFβ receptor complex with regulatory Smads, Smad 2 and 3. Moreover, the inhibitory Smad7 may recruit phosphatases and ubiquitin ligases to the activated TGFβ receptors and thereby inactivate said receptors by promoting their dephosphorylation and degradation.

The murine FIST exerts a dominant negative effect on TGFβ signaling pathway in mouse and human cells. Lysates from murine CTLL-2 cells and human NK-92 cells cultured in the presence of FIST and active TGFβ were analyzed by western blot using Smad3 and Smad2 phospho-specific antibodies. FIST does not only impair the phosphorylation status of Smad2 and Smad3 (FIG. 2A) but also induces the de novo expression of Smad7 in CTLL-2 cells (FIG. 2B). The murine CTLL-2 cells were stimulated with mFIST and controls (RPMI, recombinant (r) TGFβ, rTGFβ and FIST, IL-2, IL-2 and rTGFβ, IL-2 and s TβRIIB) for 20 minutes and cell lysates were probed with Smad2 and Smad3 phospho-specific antibodies and total Smad2/3 antibody. Similarly, murine FIST abrogates TGFβ-mediated Smad2 phosphorylation in a human NK cell line (NK-92, FIG. 2C). IL-2 as part of the fusion protein was expected to preserve its ability to recognize and to bind its specific receptors on the cell surface of IL-2 responsive cells expressing the IL-2 receptor, such as CTLL-2. As shown in FIG. 2D, FIST induces the proliferation of the IL2-dependent cell line CTLL-2. Similar results were obtained with cell lysates from splenocytes. Proliferation assay was performed by MTT incorporation using cytokine dependent cells CTLL-2, ($P>0.05$ between mFIST and IL-2). Results are shown as mean of triplicates±SEM of 1 representative experiment of 3.

IL-2/sTβRII Leads to Hyperphosphorylation of STAT1 and STAT3

Figure 3:
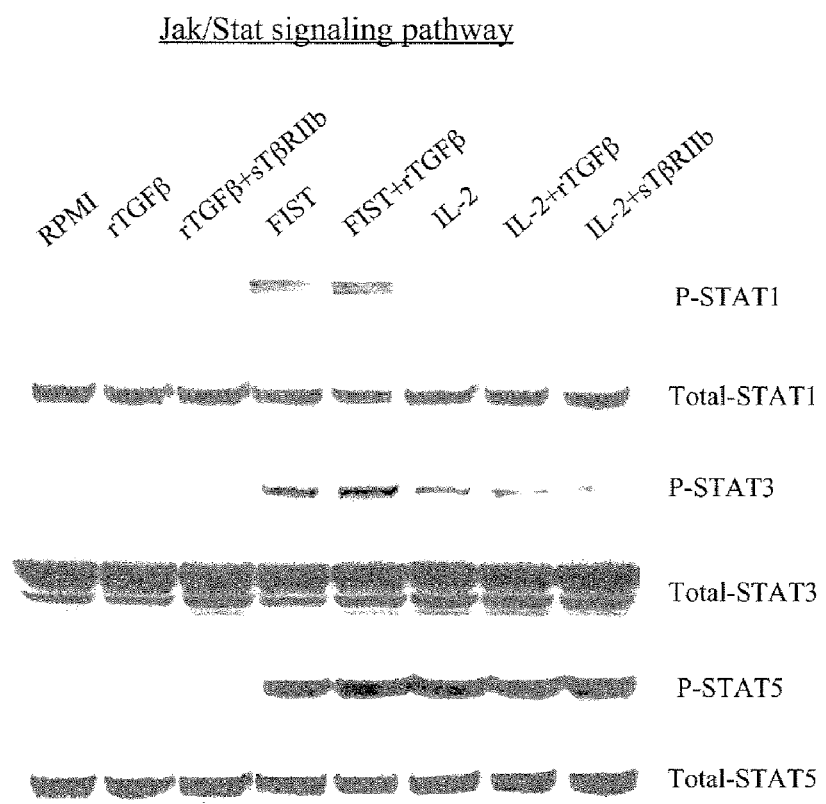
FIG. 3 shows the hyperactivation of the JAK/STAT pathway induced by mFIST compared to soluble TGFβ RIIB, IL-2 and their combinations.

These in vitro data demonstrated that FIST is a bifunctional fusokine with a dominant negative effect on TGFβ signaling with contemporaneous potent proinflammatory cytokine activity. Downstream of the IL-2 receptor, FIST promotes a synergistic hyperphosphorylation of STAT1 and STAT3. STAT3 binds to two consensus sites on the Smad7 promoter inducing its transcriptional activation. STAT1 also acts as a positive regulator of Smad7 expression via JAK1. The molecular mechanism by which FIST blocks TGFβ signaling pathway was characterized as the induction of Smad7 expression. Subsequently, the interaction of FIST with individual components of the IL-2 receptor complex (IL-2R) was assessed. The intracellular signaling of IL-2R occurs through the β chain (JAK1/STAT3) and the γ chain (JAK3/STAT5). FIST does not only induce STAT5 activation similarly to IL-2, but also promotes a distinct STAT3 and STAT1 hyperactivation in CTLL-2 (FIG. 3). Similarly, cell lysates from splenocytes were probed with the same antibodies and similar results were obtained.

FIST Induces a Potent Immune Stimulation

Previous analyses of the activation of IL-2R associated kinases, JAK1 and JAK3, and STAT5 by IL-2 in the presence or absence of TGFβ do not show any evidence of inhibition of the JAK/STAT pathway. However, TGFβ mediated inhibition seems to occur at the nuclear level of a subset of IL-2 target genes, including c-myc, cyclin D2 and cyclin E. Splenocytes cultured with FIST upregulate c-myc expression, and produce significantly greater amounts of IFNγ even in the presence of active TGFβ. In contrast, IL-2 stimulated splenocytes in the presence of active TGFβ display a dramatic downregulation of c-myc expression and IFNγ production. TGFβ is known to inhibit proinflammatory cytokine mediated-IFNγ production indirectly by downregulating the expression of T-BET, a positive regulator of IFNγ, via a Smad dependent mechanism and directly by a T-BET-independent negative regulatory effect on the IFNγ promoter.

Figure 4:
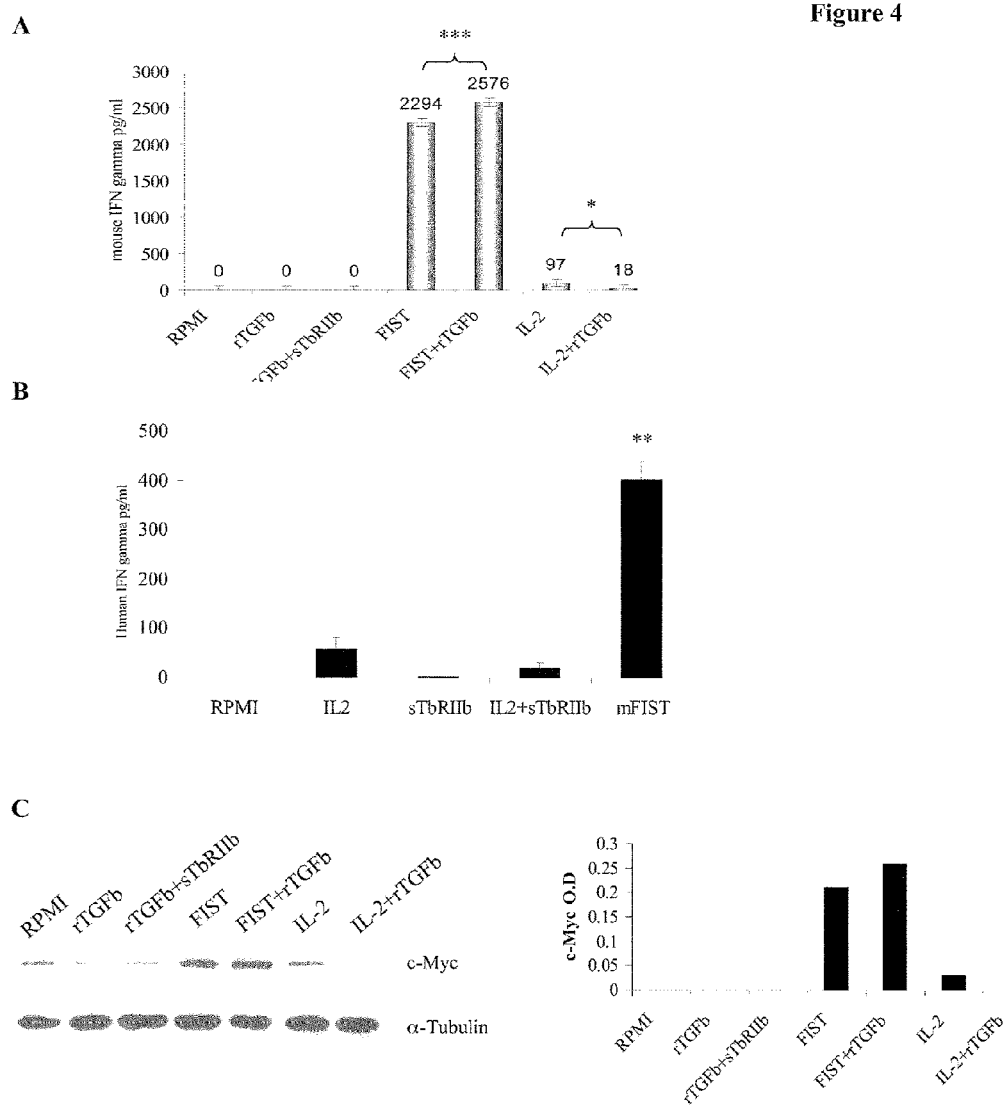
FIG. 4 shows mFIST inhibition of TGFβ-mediated suppression of IL-2 target genes IFNγ and c-Myc, IFN-γ in murine splenocytes (A), human peripheral lymphocytes (B) and the expression of c-Myc in splenocytes (C) depicted as Western Blot and quantified by optical density by mFIST compared to soluble TGFβ RIIB, IL-2 and their combinations.

As an immunostimulator, FIST primes mouse splenocytes to produce a twenty fold greater amount of IFNγ than equimolar concentrations of IL-2 and controls in 24 hours as determined by ELISA. Significant differences are indicated ($P<0.0005$: ***; $P<0.05$: *) Results are shown as mean of triplicates±SEM of one representative experiment. While IL-2 combined with TGF-β suppressed IFNγ production, active TGFβ did not interfere with the effect of FIST on IFNγ production (FIG. 4A). Acting through JAK1 and STAT1, IFNγ inhibits TGFβ-induced phosphorylation of Smad3 and its subsequent events, such as the association of Smad3 with Smad4, the nuclear translocation of this complex, and the activation of TGFβ target genes. Similarly, the murine FIST activated human peripheral blood mononuclear cells (PBMC) to produce significant greater amounts of IFNγ than equimolar concentrations of cytokine controls (FIG. 4B). FIST also upregulated the expression of c-Myc, one of IL-2 target genes, the expression of which is suppressed by TGFβ (FIG. 4C).

Tumor-derived TGFβ exerts severe suppression on several components of the immune system. For instance, TGFβ inhibits the activation, proliferation and pro-inflammatory cytokine secretion in T and B cells. It inhibits cell cytotoxicity and cytokine production in NK cells, and suppresses the expression of MHC class II and costimulatory molecules as well as cytokine secretion in dendritic cells. It also inhibits any phagocytosis dependent on IgG opsonization and IgG receptor expression, and the production of TNFα, MMP12 and chemokines in macrophages. As a TGFβ antagonist compound, FIST acts specifically on IL-2 receptor expressing cells (i.e T cells, NK and B cells), triggering signal transduction that renders them hyperactivated, demonstrated by the higher expression of the activation marker CD69, and resistant to any TGFβ effects. Consequently, these immune cell types produce significantly greater amounts of pro-inflammatory cytokines, which are essential mediators of an effective anti-tumor response. Interestingly, FIST primes B cells to secrete spectacular amounts of IFNγ.

Figure 5:
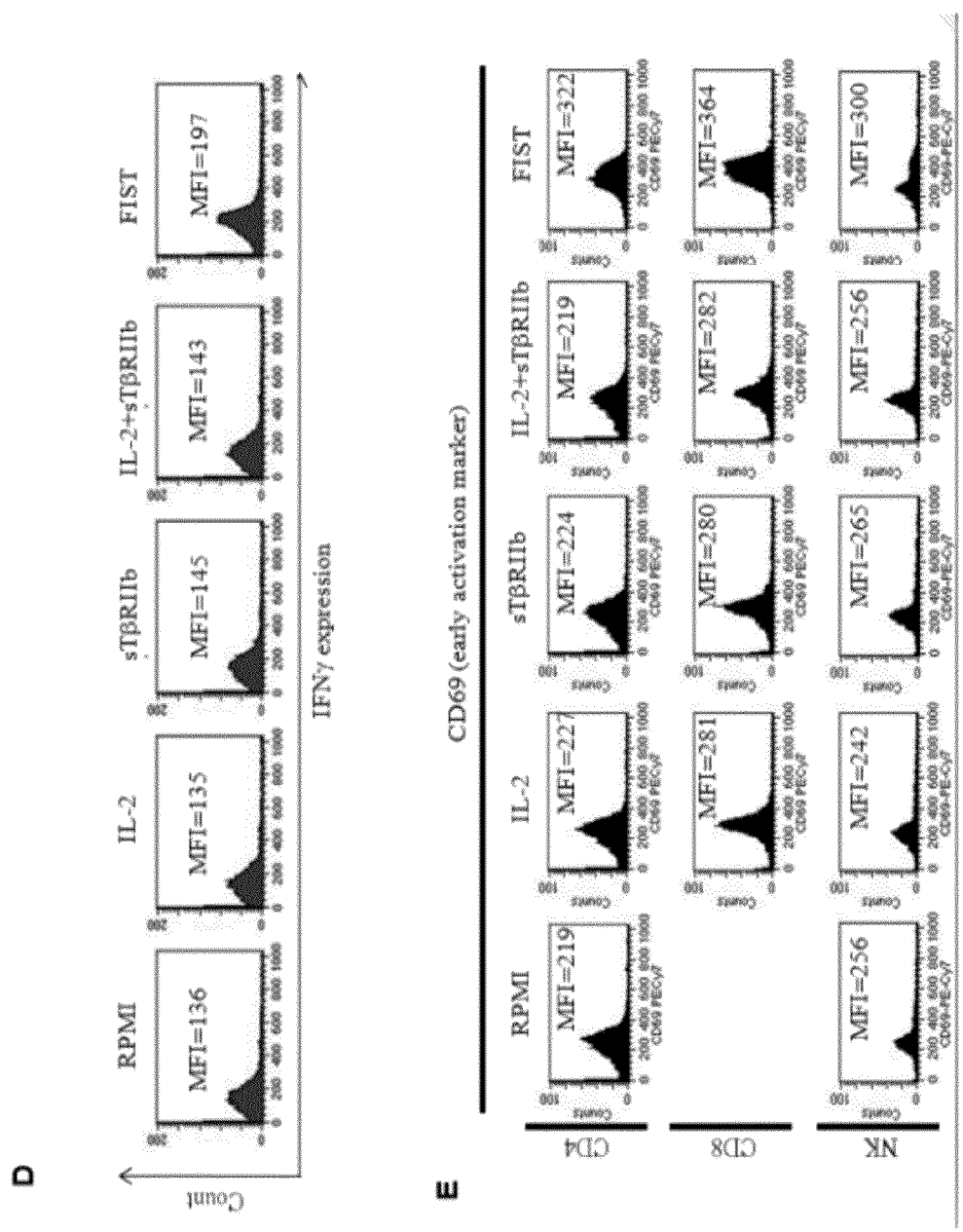
FIG. 5 shows the production of pro-inflammatory cytokines (A-D) induced by mFIST compared to soluble TGFβ RIIB, IL-2 and their combinations by ELISA in T cells (IFN-γ, A), in B cells (IFN-γ and TNF-α, B) and in NK cells (IFN-γ and GM-CSF, C) and by intracellular staining in B cells (IFN-γ, D) and the level of activation of NK, CD4 and CD8 T cells by staining with CD69, an early activation marker (E).

For the purpose of determining the types of immune cells responsive to FIST, enriched NK cells, T cells and B cells populations were cultured with FIST or equimolar concentrations of each control for 72 hours. Upon activation by FIST, T cells produced significantly higher amounts of IFNγ (FIG. 5A), B cells produced TNFα and IFNγ (FIG. 5B), and NK cells secreted GM-CSF and IFNγ (FIG. 5C). In case of B cells, intracellular staining for IFNγ confirmed that this proinflammatory cytokine was expressed by B cells and not by any other immune cell type present in the enriched cell preparation (FIG. 5D). FIST induced greater activation of CD4, CD8 T cells and NK cells. Purified CD4, CD8 and NK cells isolated from the spleen were cultured with FIST and cytokine controls for 24 hours. The activation levels of the different cell types were determined by labelling the cells with CD69 specific antibody, an early activation marker, and subsequent flow cytometry analysis. The values indicate mean fluorescence intensity. Results are shown as mean of triplicates±SEM of one representative experiment (FIG. 5E).
FIST Induces a Robust Immune Bystander Effect, Inhibits Tumor Growth and Blocks Metastases Since it is impossible to modify all pre-existing tumor cells with suicide or proinflammatory genes in situ by any contemporary gene transfer technology, an important feature to consider for cancer gene immunotherapy is the bystander effect. The secretion of FIST by genetically modified B16 cells promotes a robust anti-tumor response against non-modified tumor cells present in the tumor microenvironment. The cohort of immunocompetent C57Bl/6 mice injected with $5\times10^5$ B16 cells secreting FIST mixed with $5\times10^5$ null B16 cells displayed a higher percentage of survival (60%) than the cohort of mice implanted with $5\times10^5$ B16 cells expressing equimolar concentrations of IL-2 mixed with $5\times10^5$ null B16 cells (0%). The bystander effect in immune competent animals arises mostly from recruitment of immune cells promoting cancer specific cytolysis of local and distant tumor cells which escaped gene modification. Based on the immune infiltrated analysis, the FIST dependent bystander effect may be mediated by NK, NKT, CD8+ T and B cells. By antagonizing the TGFβ signalling pathway, FIST inhibits TGFβ dependent effects such as epithelial to mesenchymal transition (EMT), extracellular matrix breakdown, fibroblast differentiation and TGFβ dependent immunosuppression. These processes are key for tumor cell migration and metastases. FIST blocked metastases formation in a mouse model of breast cancer (equivalent to IV stage of breast cancer in human). In contrast, control groups showed multiple metastases in the lungs, liver, heart and spleen.

Figure 6:
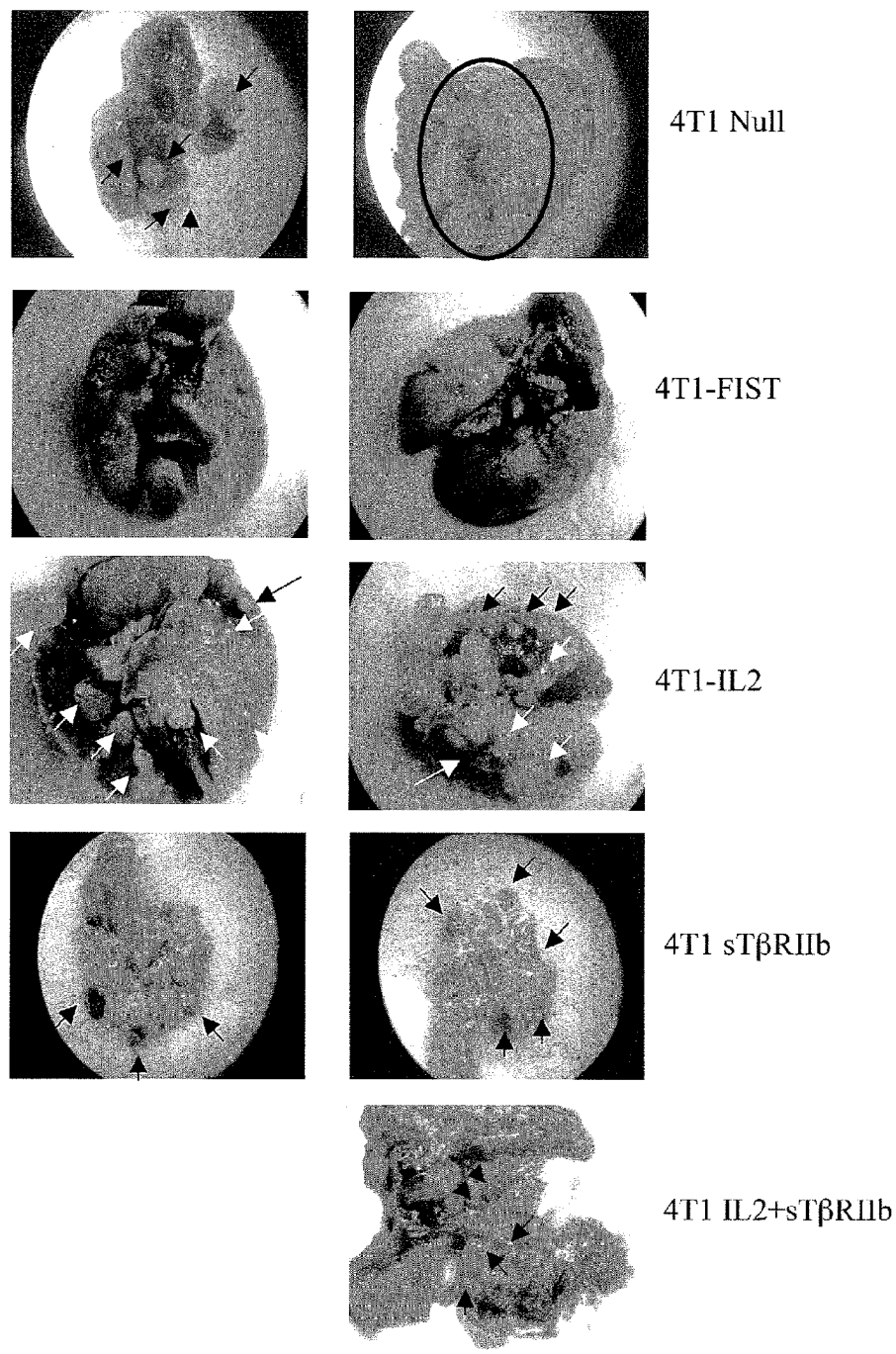
FIG. 6 shows the effect of mFIST compared to soluble TGFβ RIIB, IL-2 and their combinations in an in vivo cancer model. Panel A depicts a potent bystander anti-tumor effect in vivo, panels B and C show the significant recruitment of CD8, NK, NKT and B cells and total lymphocytes respectively, to a tumor site. Panel D demonstrates the lack of lung metastases in tumor cell lines (4T1) transduced with mFIST compared to soluble TGFβ RIIB, IL-2 and their combination.

In a mouse model of melanoma (B16F0), equimolar concentrations of FIST and IL-2 secreted by genetically modified B16 cells are equally effective in inducing a potent anti-tumor response. Consequently 10 mice were injected subcutaneously with $5\times10^5$ B16 cells expressing FIST or cytokine controls, $5\times10^5$ null B16 cells (negative control), or a mixture of both at 1:1 ratio. Survival was assessed over time and depicted in a Kaplan-Meier survival curve. FIST and IL-2, do not develop any tumors. However, the cohort of mice injected with $5\times10^5$ IL-2 secreting B16 cells mixed with $5\times10^5$ null B16 cells developed tumors as the control group injected with $5\times10^5$ null B16 cells, which indicates that the paracrine secretion of IL-2 by genetically modified B16 cells does not induce a bystander effect on null B16 cells present in the tumor microenvironment. In contrast, FIST exerts a bystander effect and protects 60% of the mice injected with mixed cells (FIG. 6A). The recruitment of $CD4^+$, $CD8^+$, $CD4^+CD25^+$, NK, NKT, B and γδ T cells to the matrigel plugs representing the tumor sites was analysed to determine which immune effector cells were implicated in FIST mediated anti-tumor responses. FIST induces greater recruitment of lymphocytes than an equimolar concentration of IL-2, as well as IL-2 combined with sTβRII (FIG. 6B). Immunocompetent C57BL/6 mice were injected subcutaneously with $1\times10^6$ genetically modified B16 cells expressing mFIST or equimolar concentrations of cytokine controls embedded in matrigel. Implants were retrieved 7 days post tumor implantation and digested with collagenase to collect infiltrated immune cells, which were analyzed by flow cytometry using antibodies specific for each cell surface marker. Results are shown as mean of triplicates±SEM of one representative experiment Specifically, a significant recruitment of NK, NKT, B and $CD8^+$ T cells in the tumor site was observed and depicted as the total number of recruited lymphocytes (FIG. 6C). The anti-metastatic potential of FIST was tested with 4T1 cells, a cell line generating a metastatic model of stage IV breast cancer, transduced with retroviruses expressing FIST and the cytokine controls. These genetically modified 4T1 cells were implanted subcutaneously into immunocompetent BALB/c mice (10 mice per group). Mice were sacrificed two months later and no tumor metastases were observed in the group treated with FIST. In contrast control groups showed multiple metastases in lungs, liver, heart and spleen. The comparison between treatments is demonstrated by the number of lung metastases that developed and which are shown in the FIG. 6D).

The Murine FIST (mFIST) and Human FIST (hFIST) Inhibit Angiogenesis

Figure 7:
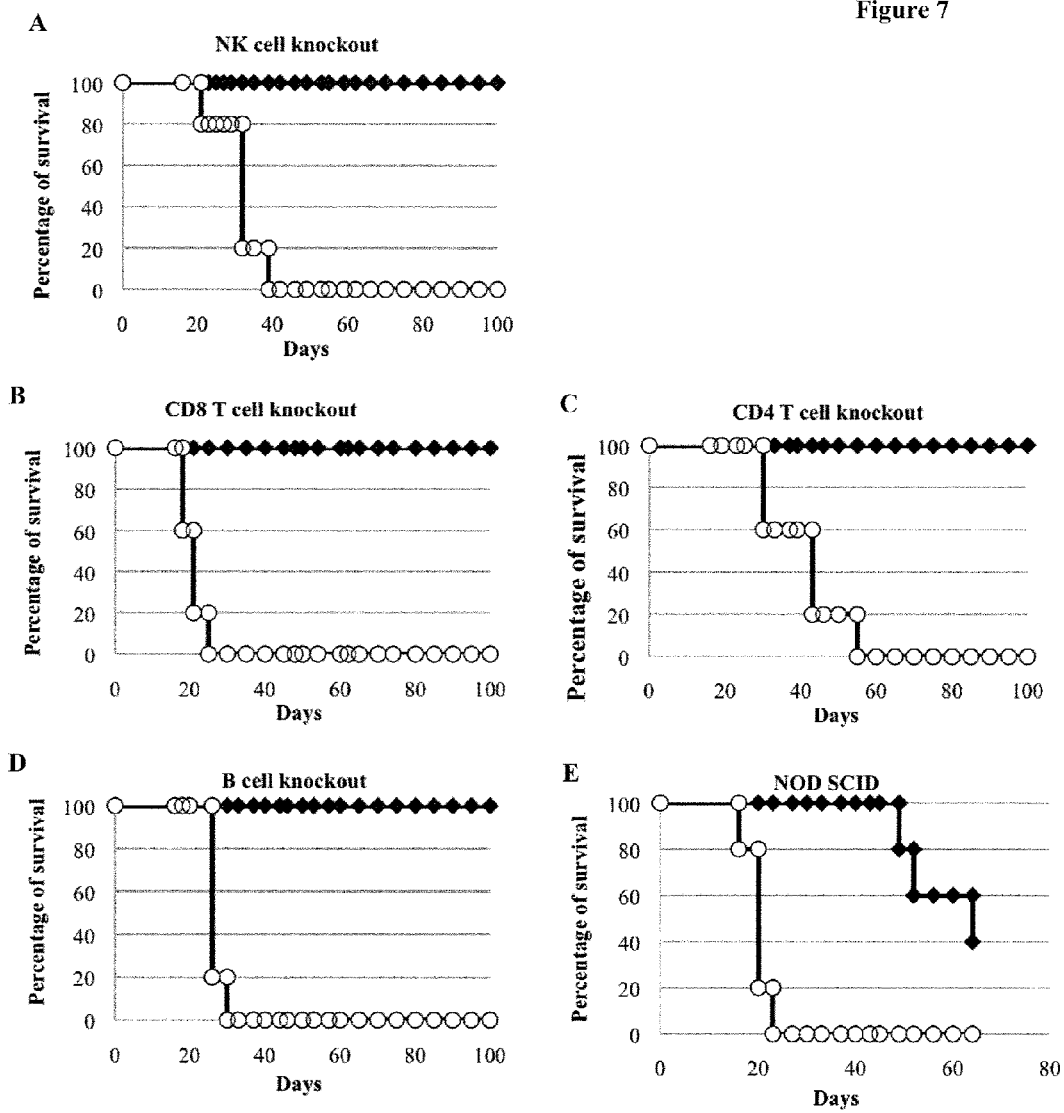
FIG. 7 shows Kaplan-Meier curves of various mouse strains injected with 5×10$^5$ B16 null (●) or B16 cells expressing murine FIST (●) (A) Beige mice, (B) CD8 T cells knockout mice, (C) CD4 T cells knockout mice, (D) B cell knockout mice and (E) NOD SCID mice.

FIST dependent effects are not restricted to the activity of one immune cell type since FIST acts on all cells that express IL-2 receptor. Surprisingly, CD4+ T cells, CD8+ T cells, B cell knockout and beige mice do not develop tumors, whereas NOD SCID mice implanted with B16 cells expressing FIST developed tumors. These results indicate that the immune response is implicated in FIST mediated anti-cancer effects and the deficiency of one immune cell type is not sufficient to inhibit tumor progression. Interestingly, NOD SCID mice implanted with B16 cells expressing FIST show a significant delay of tumor growth. The necrotic appearance of the tumors expressing mFIST in NOD SCID mice suggests that FIST may act as an anti-angiogenic compound in vivo.

mFIST induces a robust activation and recruitment of NK, NKT, T and B cells in vitro and in vivo. These immune cell types express the IL-2 receptor and therefore are responsive to FIST. For the in vivo investigation on which cell type is the essential mediator of FIST anti-tumor effect, $5 \times 10^5$ null B16 cells or B16 cells expressing mFIST subcutaneously were implanted into different immunodeficient mice, including NK cell deficient beige mice (FIG. 7A), CD8 knock out mice (FIG. 7B), CD4 knock out mice (FIG. 7C), B cells knockout mice (FIG. 7D), and NOD SCID mice (FIG. 7E). mFIST protected CD4 and CD8 T cell knock out mice, B cells knockout mice and beige mice from tumor development. In contrast 60% of NOD SCID mice developed big tumors and were sacrificed although they showed a significant delay in tumor growth compared to the control at 60 days post tumor implantation (FIG. 7E).

Tumor angiogenesis is regulated by a network of growth factors including members of the TGFβ family. The mechanism by which TGFβ induces tumor angiogenesis is not well defined, but presumably is the product of direct and indirect effects. Directly, TGFβ can activate endothelial cell (EC) proliferation and migration. In addition, TGFβ induces capillary formation when EC are cultured on a collagen matrix and promotes angiogenesis in vivo in the chicken chorioallantoic membrane assay. Indirectly, TGFβ induces VEGF expression in various cells in a tumor microenvironment, such as tumor cells, macrophages and stromal fibroblasts. In addition, TGFβ regulates the expression of various extracellular matrix components that play a key role in both the initiation and the resolution phase of tumor angiogenesis. As antagonists of the TGFβ signalling pathway, mFIST as well as hFIST inhibit HUVEC tube formation in vitro indicative of angiogenesis progression. Interestingly, tumors from NOD SCID mice implanted with B16 cells expressing FIST were very necrotic. These results suggest that besides targeting the immune system, FIST may also influence tumor-derived angiogenesis. As verification of this hypothesis, in vitro angiogenesis assays were performed using human umbilical vein endothelial cells (HUVEC). Angiogenesis scores were defined based on the numbers and sizes of polygons formed, capillary thickness and cells alignment and fusion. While both mFIST as well as hFIST inhibit angiogenesis (score 0), HUVEC tube formation were observed in the control samples (scores for each sample are indicated in FIG. 8). HUVEC cells ($3 \times 10^4$) were seeded on matrigel containing laminin, collagen type IV, heparin sulfate proteoglycans, entactin and nidogen and were cultured in the presence of the 5 pmols of murine FIST (mFIST), human FIST (hFIST) or the respective controls for 16 hours. Angiogenesis progression was determined based on the number and size of polygons formed, capillary thickness and cell alignment and fusion. HUVEC cells cultured in the presence of the mFIST or hFIST displayed the lowest capacity to form endothelial cell tubes on matrigel (score 0). Score interpretation: Closed polygons formed (A): 1—only few but big in size, 2—many and big+ few and small, 3—many and various sizes. Capillary (B): 1—thick, 2—medium, 3—thin. Individual cells were separated (C): 1—many individual cells, 2—few individual cells, 3—all cells align themselves.

Ex Vivo Stimulated mFIST B Cells Act as Potent APC In Vitro and In Vivo and Protect Mice from Tumor Challenge FIST can be also used as an ex vivo immunostimulator to induce a potent B cell activation and proliferation. B cells cultured in the presence of FIST show a dramatic morphologic change characterized by a granular appearance and an increase in the cell size. Moreover, FIST-stimulated B cells upregulate the expression of MHC class II, activation markers such as CD69, and co-stimulatory molecules. In addition, the increased expression of the IL-2 receptor α chain, CD25, suggests that FIST-stimulated B cells become highly responsive to IL-2. This phenotype indicates that FIST-stimulated B cells may behave as effective antigen presenting cells (APC). Indeed, in vitro FIST-stimulated B cells pulsed with ovalbumin (OVA) activate CD4+ and CD8+ T cells to secrete significantly greater amounts of IL-2 and IFNγ. Similarly, FIST-stimulated and OVA-pulsed B cells protect mice implanted with E.G7 cells from tumor development. These new features acquired by FIST-stimulated B cells suggest that FIST is suppressing the TGFβ pathway in B cells. Previous studies reported that TGFβ can inhibit the proliferation of both murine and human B cells activated by a variety of stimuli such as mitogen and ligation of CD40, these inhibitory properties are associated with a decrease in c-Myc expression. In addition, TGFβ increases the rate of apoptosis of normal resting B cells via caspase 3 and inhibits the expression of class II MHC transactivator (CIITA) and thus MHC class II and the class switching for the majority of immunoglobulin isotypes except for IgA.

Figure 9:
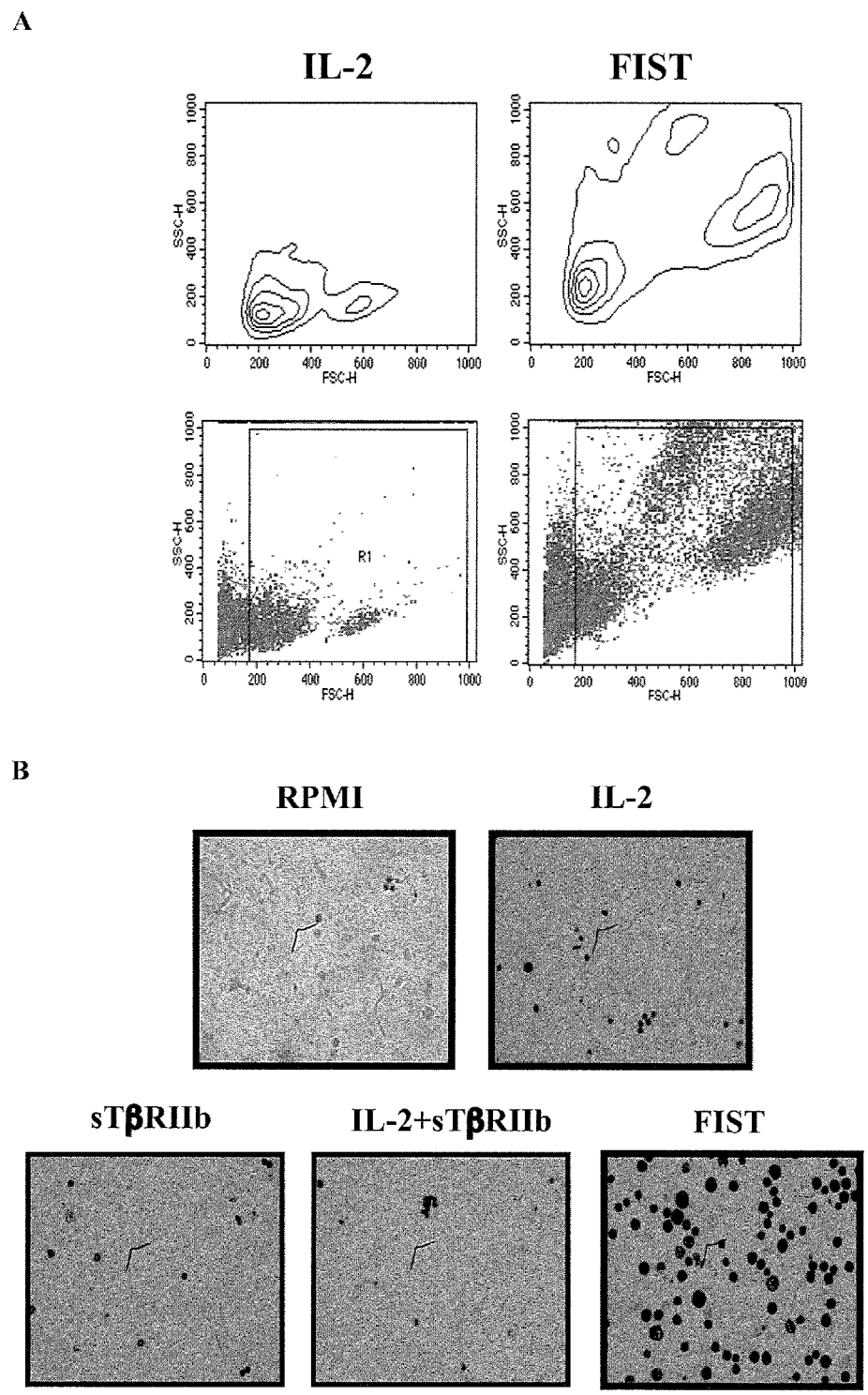
FIG. 9 shows the phenotypic analysis of ex vivo mFIST stimulated B cells by FACS (A and C) and H&E staining (B).
Figure 9:
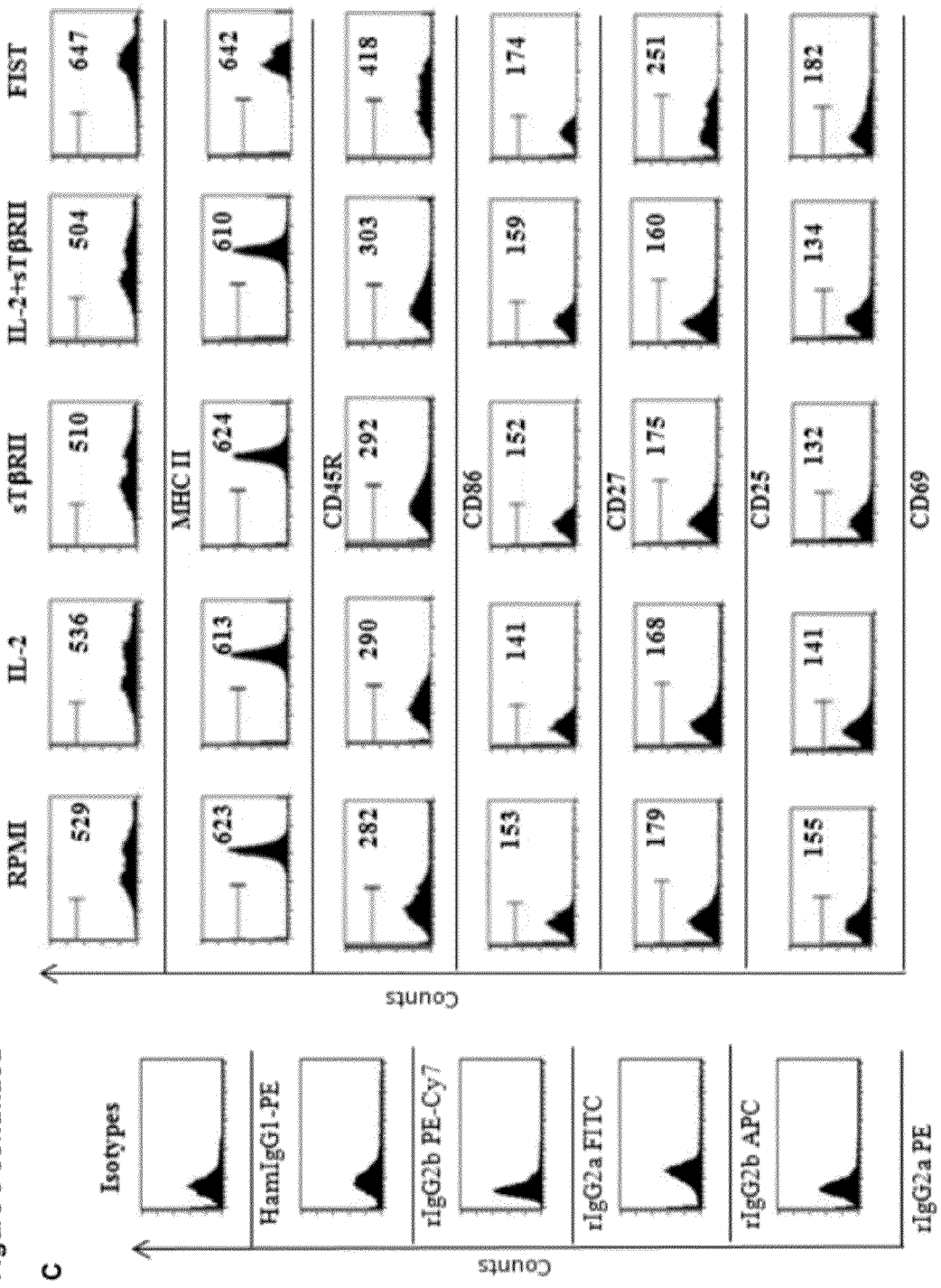

B cells cultured with mFIST for five days undergo a differentiation process characterized by phenotypic changes including the increase in size and granularity as confirmed by fluorescence activated cell sorting (FIG. 9A) and hematoxylin and eosin staining (FIG. 9B), as well as the upregulation of the expression of MHC class II, costimulatory molecules, such as CD45R, CD86 and CD27, and general activation markers, such as CD69 and CD25, the IL-2 receptor 60 chain (FIG. 9C).

This new phenotype suggests that FIST stimulated B cells may act as effective antigen presenting cells (APC). B cells stimulated by FIST in vitro and pulsed with ovalbumin (OVA) primed CD8+ and CD4+ T cells of OTI 1 and OTI 2 transgenic mice, respectively, to secrete significant amounts of IL-2 and IFNγ. OTI 1 and OTI 2 T cells recognize OVA 257-264 residues in the context of H2K$^b$ (MHCI) or 323-339 residues in the context of I-A$^b$ (MHCII), respectively (FIG. 10A). B cells stimulated by FIST in vivo also act as potent APC, which protect immunocompetent mice from a tumor challenge (FIG. 10B). These results indicate that ex vivo FIST-stimulated B cells differentiate into a more powerful APC.

Human FIST Inhibits Angiogenesis and Induces a High Production of IFNγ

As characterized in FIG. 11, human FIST induces the proliferation of IL-2 dependent CTLL-2 cells similar to mFIST (FIG. 11C), and the significantly increased production of IFNγ compared to cytokine controls (FIG. 11D), and inhibits angiogenesis similar to mFIST (FIG. 8).

Material and Methods

Animals, Cell Lines, Recombinant Proteins and Antibodies and ELISA Kits

All mice were female 6 to 8 weeks old (Jackson Laboratory, Bar Harbor, Me.). The 4T1 mouse breast cancer cells were maintained in Dulbecco's modified Eagle's medium (Wisent Technologies, Rocklin, Calif.), supplemented with 10% fetal bovine serum (Wisent Technologies) and 50 U/ml Pen/Strep (Wisent Technologies). The cell lines CTLL-2 and JAWSII (American Type Culture Collection [ATCC], Manassas, Va.) were grown according to ATCC's recommendations. Recombinant mouse and human TGFβ, IL-2 and soluble TGFβ receptor II (TβRII) were obtained from R&D Systems, Minneapolis, Minn.; antiphosphorylated SMAD2, SMAD3, STAT1, STAT3, STAT5 antibodies (Cell Signalling Technology, Danvers, Mass.); α-tubulin and Smad7 antibodies (Santa Cruz Biotechnology, Santa Cruz, Calif.). Specific antibodies for immune cell surface markers (CD4, CD8, CD25, CD19 and NK1.1), costimulatory molecules on B cells (CD45R, CD27, CD86, CD25), MHC II, as well as activation marker (CD69) and isotype control antibodies for flow cytometry were obtained from BD Biosciences, San Diego, Calif. The enzyme-linked immunosorbent assay (ELISA) kit for mouse and human IFN-γ, mouse IL-2, human IL-2, mouse TNFα and mouse GM-CSF were obtained from eBiosciences.

Vectors Construct

The mouse IL-2 cDNA (Invivogen San Diego, Calif.) was modified to remove the 3' nucleotides encoding STOP codons and subsequently cloned in frame with the cDNA encoding the mouse TGFβ receptor IIB ectodomain (Invivogen San Diego, Calif.) to generate the cDNA for IL-2/sTβRIIB fusokine. The cDNAs of both components were incorporated into a bicistronic retrovector allowing the expression of the fusokines and a GFP reporter. Human FIST was generated following the same cloning strategy.

Fusokine Expression and Functional Assays

Infectious retroparticles encoding IL-2/sTβRIIB were generated with 293-GP2 packaging cells (Clontech, Mountain View, Calif.) and concentrated retroviruses were used to genetically modify 4T1 breast cancer cells (animal model for stage IV human breast cancer) and B16 melanoma cells. To test the bioactivity of IL-2/sTβRIIB, the IL-2 responsive CTLL-2 cell line was plated at density of $10^5$ cells per well in a 96-well plate and treated with increasing concentrations of cytokines for 72 hours. Cell proliferation was assessed with a 3-(4,5-dimethylhiazol-2-yl)-2,5-diphenyltetrazolium (MTT) assay. Co-immunoprecipitation assays were performed by using anti-IL-2 antibody bound protein G beads and precipitates were analyzed by immunoblot with a sTβRII specific antibody.

Immune Cell Isolation

Enriched T, B and NK cell populations were obtained from splenocytes of immunocompetent mice. Splenocytes were resuspended in 2 ml of PBS containing rat serum and non-desired cells were depleted by magnetic cell sorting selection according to the manufacturer's recommendation (Stem Cell Technology). The purity of each population assessed by flow cytometry using specific conjugated antibodies for the immune cell markers (CD4, CD3, CD8, NK1.1 and CD19 for B cells 93%, NK cells 96% and T cells 97%).

Intracellular Signaling

For signaling analysis, media conditioned by stably transfected 293 T cells expressing murine FIST, as well as media conditioned by non transfected cells containing equimolar concentration of cytokine controls (IL-2, sTβRIIB or IL-2 combined with sTβRIIB, 5 pmol each) were added to $5\times10^6$ CTLL-2 and NK-92 cells for 20 minutes before being lysed and probed by Western blot (WB) with rabbit anti-phosphorylated Stat1, Stat3 and Stat5, Smad3 and Smad2. Antibodies against total proteins were used as loading controls.

Immune Effector Infiltration Analysis

One million cytokine-secreting B16 cells (in 50 ul of PBS) were mixed with 500 ul of Matrigel (BD Biosciences) at 4° C. and injected subcutaneously in C57Bl/6 mice (n=4 per group). After 7 days, implants were surgically removed and incubated for 30 minutes with a solution of 1.6 mg/mL collagenase type IV (Sigma-Aldrich, Oakville, Ontario, Canada) and 200 ug/mL DNaseI (Sigma-Aldrich) in PBS. After incubation with anti-Fc III/II mAb (clone 2.4G2; BD PharMingen, San Diego, Calif.) for 1 hour, cells were incubated for 1 hour at 4° C. with anti-mouse CD4, CD8, CD25, CD19, γδ T cells and NK1.1 antibodies or the appropriated isotypic controls for one hour. The expression of these cell surface markers was determined by using FACS Calibur cytometer (BD) and analyzed using Cellquest software (BD).

Murine B16 and 4T1 Tumor Implantation in Immunocompetent BALB/c Mice

Non-modified and genetically modified cytokine-secreting B16 and 4T1 cells (B16-FIST:10 pmol/$10^6$ cells, 4T1-FIST: $4\times10^{-3}$ pmol/$10^6$ cells as well as equimolar concentration of cytokine control in 24 hours) were injected subcutaneously in C57Bl/6 or BalB/c mice respectively. Tumor volume and survival was monitored over time. BalB/c mice implanted with 4T1 cells were screened for the presence of metastases in the liver, lungs, spleen, lymph nodes and brain.

Murine B16F0 Tumor Implantation in Immunodeficient Mice $5\times10^5$ FIST secreting or GFP-expressing B16 cells were injected subcutaneously in 10 mice per group of immunocompromised nonobese diabetic-severe combined immunodeficient (NOD-SCID) mice, CD4 T cell knockout, CD8 T cell knockout, B cell knockout and beige mice respectively, and tumor growth and survival was monitored over time.

In Vitro Angiogenesis Assay

Ninety-six-well plates were first coated at 37° C. for 2 hours with a matrix containing laminin, collagen type IV, heparin sulfate proteoglycans, entactin and nidogen (chemicon). $3\times10^4$ HUVECS were seeded then in each and were incubated in the presence of FIST or the controls for 16 hours. A numerical score was assigned to each condition according to the degree of angiogenesis progression, from 0 (no angiogenesis to 9 (high angiogenic activity). The pattern association criterion was defined by the number and size of polygons formed, capillary thickness and cell alignment and fusion.

In Vitro APC Assay and In Vivo APC Activity of FIST-Stimulated B Cells

APC assays were performed using purified B cells from C57BL/6 immunocompetent mice. B as antigen presenting cells (APC) were stimulated for three days with 1 pmol/ml of FIST or equimolar concentrations of cytokine controls (IL-2, sTβRIIB and IL2 combined with sTβRIIB), washed and pulsed with OVA for an additional 24 hours. Subsequently, $5\times10^4$ B cells were washed three times with PBS and co-cultured with $1\times10^5$ CD8 or CD4 T cells isolated from OTI I and OTI II mice respectively. After 24 hours, supernatants were collected and IL-2 and IFNγ production was assessed as readout of T cells activation using IL-2 and IFNγ ELISA kits (eBiosciences). In order to determine the ability of FIST-stimulated B cells in vivo to act as potent APC, C57BL/6 immunocompetent mice were injected with $1\times10^5$ of FIST-, IL-2-, sTβRIIB- or the combination of IL-2 and sTβRIIB-stimulated B cells, three weeks later mice were boosted with equal doses of cytokine stimulated B cells, and one week later were challenged with 5×10⁵ lymphoma cell line (E.G7). Tumor volume and survival was assessed over time.
Statistical Analysis
P values were calculated using the paired Student t test.

Example 2

The human FIST sequence was modified to improve its yield (FIG. 12c). The bolded amino acid sequence as shown in FIG. 12a corresponding to the transmembrane domain of sTβRII was removed to improve the secretion of the protein (as shown in FIG. 12b). This modification did not affect the bioactivity of the protein.

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

Table of Sequences:

```
DNA Sequence of mouse IL2/sTβRII fusion protein
                                          (SEQ ID NO: 1)
ATGTACAGCATGCAGCTCGCATCCTGTGTCACATTGACACTTGTGCTC
CTTGTCAACAGCGCACCCACTTCAAGCTCCACTTCAAGCTCTACAGCG
GAAGCACAGCAGCAGCAGCAGCAGCAGCAGCAGCAGCAGCAGCACCTG
GAGCAGCTGTTGATGGACCTACAGGAGCTCCTGAGCAGGATGGAGAAT
TACAGGAACCTGAAACTCCCCAGGATGCTCACCTTCAAATTTTACTTG
CCCAAGCAGGCCACAGAATTGAAAGATCTTCAGTGCCTAGAAGATGAA
CTTGGACCTCTGCGGCATGTTCTGGATTTGACTCAAAGCAAAAGCTTT
CAATTGGAAGATGCTGAGAATTTCATCAGCAATATCAGAGTAACTGTT
GTAAAACTAAAGGGCTCTGACAACACATTTGAGTGCCAATTCGATGAT
GAGTCAGCAACTGTGGTGGACTTTCTGAGGAGATGGATAGCCTTCTGT
CAAAGCATCATCTCAACAGCTAGCGCTACCGGACTCAGATCTCGACGC
ATCGCCAGCACGATCCCGCCGCACGTTCCCAAGTCGGATGTGGAAATG
GAAGCCCAGAAAGATGCATCCATCCACCTAAGCTGTAATAGGACCATC
CATCCACTGAAACATTTTAACAGTGATGTCATGGCCAGCGACAATGGC
GGTGCGGTCAAGCTTCCACAGCTGTGCAAGTTTTGCGATGTGAGACTG
TCCACTTGCGACAACCAGAAGTCCTGCATGAGCAACTGCAGCATCACG
GCCATCTGTGAGAAGCCGCATGAAGTCTGCGTGGCCGTGTGGAGGAAG
AACGACAAGAACATTACTCTGGAGACGGTTTGCCACGACCCCAAGCTC
ACCTACCACGGCTTCACTCTGGAAGATGCCGCTTCTCCCAAGTGTGTC
ATGAAGGAAAAGAAAAGGGCGGGCGAGACTTTCTTCATGTGTGCCTGT
AACATGGAAGAGTGCAACGATTACATCATCTTTTCGGAAGAATACACC
ACCAGCAGTCCCGACCTGTTGTTGGTCATTATCCAAGTGACGGATCCC
CTTTG Amino-acid sequence of mouse IL-2/sTβRII fusion
protein
                                          (SEQ ID NO: 2)
MYSMQLASCVTLTLVLLVNSAPTSSSTSSSTAEAQQQQQQQQQQQQHL
EQLLMDLQELLSRMENYRNLKLPRMLTFKFYLPKQATELKDLQCLEDE
LGPLRHVLDLTQSKSFQLEDAENFISNIRVTVVKLKGSDNTFECQFDD
ESATVVDFLRRWIAFCQSIIST ASATGLRSRRIASTIPPHVPKSDVEM
EAQKDASIHLSCNRTIHPLKHFNSDVMASDNGGAVKLPQLCKFCDVRL
STCDNQKSCMSNCSITAICEKPHEVCVAVWRKNDKNITLETVCHDPKL
TYHGFTLEDAASPKCVMKEKKRAGETFFMCACNMEECNDYIIFSEEYT
TSSPDLLLVIIQVTDPL
```

The underlined portion above is the linker. In the above fusion, the last 3 amino acids of IL-2 are deleted and the last 3 amino acids of the fusion protein are from the carboxy-terminus of mouse GM-CSF. The ectodomain is the alternatively spliced form of the extracellular domain of the Type II TGFβ Receptor, which was used to make this soluble form.

```
DNA sequence of human IL-2/sTβRIIB
                                          (SEQ ID NO: 3)
ATGTACAGGATGCAACTCCTGTCTTGCATTGCACTAAGTCTTGCACTT
GTCACAAACAGTGCACCTACTTCAAGTTCTACAAAGAAAACACAGCTA
CAACTGGAGCATTTACTTCTGGATTTACAGATGATTTTGAATGGAATT
AATAATTACAAGAATCCCAAACTCACCAGGATGCTCACATTTAAGTTT
TACATGCCCAAGAAGGCCACAGAACTGAAACATCTTCAGTGTCTAGAA
GAAGAACTCAAACCTCTGGAGGAAGTGCTAAATTTAGCTCAAAGCAAA
AACTTTCACTTAAGACCCAGGGACTTAATCAGCAATATCAACGTAATA
GTTCTGGAACTAAAGGGATCTGAAACAACATTCATGTGTGAATATGCT
GATGAGACAGCAACCATTGTAGAATTTCTGAACAGATGGATCCTCAGG
GGCCTGTGGCCGCTGCACATCGTCCTGTGGACGCGTATCGCCAGCACG
ATCCCACCGCACGTTCAGAAGTCGGATGTGGAAATGGAGGCCCAGAAA
GATGAAATCATCTGCCCCAGCTGTAATAGGACTGCCCATCCACTGAGA
CATATTAATAACGACATGATAGTCACTGACAACAACGGTGCAGTCAAG
TTTCCACAACTGTGTAAATTTTGTGATGTGAGATTTTCCACCTGTGAC
AACCAGAAATCCTGCATGAGCAACTGCAGCATCACCTCCATCTGTGAG
AAGCCACAGGAAGTCTGTGTGGCTGTATGGAGAAAGAATGACGAGAAC
ATAACACTAGAGACAGTTTGCCATGACCCCAAGCTCCCCTACCATGAC
TTTATTCTGGAAGATGCTGCTTCTCCAAAGTGCATTATGAAGGAAAAA
AAAAGCCTGGTGAGACTTTCTTCATGTGTTCCTGTAGCTCTGATGAG
TGCAATGACAACATCATCTTCTCAGAAGAATATAACACCAGCAATCCT
GACTGGGAGCCAGTCCAGGAGTGAG Amino acid sequence of human IL-2/sTβRIIB
                                          (SEQ ID NO: 4)
MYRMQLLSCIALSLALVTNSAPTSSSTKKTQLQLEHLLLDLQMILNGI
NNYKNPKLTRMLTFKYMPKKATELKHLQCLEEELKPLEEVLNLAQSK
NFHLRPRDLISNINVIVLELKGSETTFMCEYADETATIVEFLNRWILR
```

-continued

GLWPLHIVLWTRIASTIPPHVQKSDVEMEAQKDEIICPSCNRTAHPLR

HINNDMIVTDNNGAVKFPQLCKFCDVRFSTCDNQKSCMSNCSITSICE

KPQEVCVAVWRKNDENITLETVCHDPKLPYHDFILEDAASPKCIMKEK

KKPGETFFMCSCSSDECNDNIIFSEEYNTSNPDFWEPVQE

The underlined portion above is the linker. In the above fusion, the last 11 amino acids of IL-2 are deleted and the last 7 amino acids are from the carboxy-terminus of human GM-CSF.

Verified DNA Sequence of mouse IL2/sTβRII fusion protein
(SEQ ID NO: 5)
ATGTACAGCATGCAGCTCGCATCCTGTGTCACATTGACACTTGTGCTCC

TTGTCAACAGCGCACCCACTTCAAGCTCCACTTCAAGCTCTACAGCGGA

AGCACAGCAGCAGCAGCAGCAGCAGCAGCAGCAGCAGCACCTGGAG

CAGCTGTTGATGGACCTACAGGAGCTCCTGAGCAGGATGGAGAATTACA

GGAACCTGAAACTCCCCAGGATGCTCACCTTCAAATTTTACTTGCCCAA

GCAGGCCACAGAATTGAAAGATCTTCAGTGCCTAGAAGATGAACTTGGA

CCTCTGCGGCATGTTCTGGATTTGACTCAAAGCAAAAGCTTTCAATTGG

AAGATGCTGAGAATTTCATCAGCAATATCAGAGTAACTGTTGTAAAACT

AAAGGGCTCTGACAACACATTTGAGTGCCAATTCGATGATGAGTCAGCA

ACTGTGGTGGACTTTCTGAGGAGATGGATAGCCTTCTGTCAAAGCATCA

TCTCAACAGCTAGCACGATCCCGCCGCACGTTCCCAAGTCGGATGTGGA

AATGGAAGCCCAGAAAGATGCATCCATCCACCTAAGCTGTAATAGGACC

ATCCATCCACTGAAACATTTTAACAGTGATGTCATGGCCAGCGACAATG

GCGGTGCGGTCAAGCTTCCACAGCTGTGCAAGTTTTGCGATGTGAGACT

GTCCACTTGCGACAACCAGAAGTCCTGCATGAGCAACTGCAGCATCACG

GCCATCTGTGAGAAGCCGCATGAAGTCTGCGTGGCCGTGTGGAGGAAGA

ACGACAAGAACATTACTCTGGAGACGGTTTGCCACGACCCCAAGCTCAC

CTACCACGGCTTCACTCTGGAAGATGCCGCTTCTCCCAAGTGTGTCATG

AAGGAAAAGAAAAGGGCGGGCGAGACTTTCTTCATGTGTGCCTGTAACA

TGGAAGAGTGCAACGATTACATCATCTTTTCGGAAGAATACACCACCAG

CAGTCCCGACCTGTTGTTGGTCATTATCCAAGTGACGGATCCCCTTTG

Verified Amino-acid sequence of mouse IL-2/sTβRII fusion protein
(SEQ ID NO: 6)
MYSMQLASCVTLTLVLLVNSAPTSSSTSSSTAEAQQQQQQQQQQQHLE

QLLMDLQELLSRMENYRNLKLPRMLTFKFYLPKQATELKDLQCLEDELG

PLRHVLDLTQSKSFQLEDAENFISNIRVTVVKLKGSDNTFECQFDDESA

TVVDFLRRWIAFCQSIISTASTIPPHVPKSDVEMEAQKDASIHLSCNRT

IHPLKHFNSDVMASDNGGAVKLPQLCKFCDVRLSTCDNQKSCMSNCSIT

AICEKPHEVCVAVWRKNDKNITLETVCHDPKLTYHGFTLEDAASPKCVM

KEKKRAGETFFMCACNMEECNDYIIFSEEYTTSSPDLLLVIIQVTDPL

-continued
DNA sequence of modified human IL-2/sTβRIIB
(SEQ ID NO: 7)
ATGTACAGGATGCAACTCCTGTCTTGCATTGCACTAAGTCTTGCACTTG

TCACAAACAGTGCACCTACTTCAAGTTCTACAAAGAAAACACAGCTACA

ACTGGAGCATTTACTTCTGGATTTACAGATGATTTTGAATGGAATTAAT

AATTACAAGAATCCCAAACTCACCAGGATGCTCACATTTAAGTTTTACA

TGCCCAAGAAGGCCACAGAACTGAAACATCTTCAGTGTCTAGAAGAAGA

ACTCAAACCTCTGGAGGAAGTGCTAAATTTAGCTCAAAGCAAAAACTTT

CACTTAAGACCCAGGGACTTAATCAGCAATATCAACGTAATAGTTCTGG

AACTAAAGGGATCTGAAACAACATTCATGTGTGAATATGCTGATGAGAC

AGCAACCATTGTAGAATTTCTGAACAGATGGATCCGTATCGCCAGCACG

ATCCCACCGCACGTTCAGAAGTCGGATGTGGAAATGGAGGCCCAGAAAG

ATGAAATCATCTGCCCCAGCTGTAATAGGACTGCCCATCCACTGAGACA

TATTAATAACGACATGATAGTCACTGACAACAACGGTGCAGTCAAGTTT

CCACAACTGTGTAAATTTTGTGATGTGAGATTTTCCACCTGTGACAACC

AGAAATCCTGCATGAGCAACTGCAGCATCACCTCCATCTGTGAGAAGCC

ACAGGAAGTCTGTGTGGCTGTATGGAGAAAGAATGACGAGAACATAACA

CTAGAGACAGTTTGCCATGACCCCAAGCTCCCCTACCATGACTTTATTC

TGGAAGATGCTGCTTCTCCAAAGTGCATTATGAAGGAAAAAAAAAAGCC

TGGTGAGACTTTCTTCATGTGTTCCTGTAGCTCTGATGAGTGCAATGAC

AACATCATCTTCTCAGAAGAATATAACACCAGCAATCCTGAATTCTGGG

AGCCAGTCCAGGAGTGA

Amino acid sequence of modified human IL-2/sTβRIIB
(SEQ ID NO: 8)
MYRMQLLSCIALSLALVTNSAPTSSSTKKTQLQLEHLLLDLQMILNGIN

NYKNPKLTRMLTFKFYMPKKATELKHLQCLEEELKPLEEVLNLAQSKNF

HLRPRDLISNINVIVLELKGSETTFMCEYADETATIVEFLNRWIRIAST

IPPHVQKSDVEMEAQKDEIICPSCNRTAHPLRHINNDMIVTDNNGAVKF

PQLCKFCDVRFSTCDNQKSCMSNCSITSICEKPQEVCVAVWRKNDENIT

LETVCHDPKLPYHDFILEDAASPKCIMKEKKKPGETFFMCSCSSDECND

NIIFSEEYNTSNPEFWEPVQE

References:
- Del Re E, Babitt J L, Pirani A, Schneyer A L, Lin H Y. (2004). J Biol Chem. May 21; 279 (21), 22765-72.
- Ge R, Rajeev V, Ray P, Lattime E, Rittling S, Medicherla S, Protter A, Murphy A, Chakravarty J, Dugar S, Schreiner G, Barnard N and Reiss M. (2006). Clin Cancer Res, 12, 4315-4330.
- Gorelik L and Flavell R A. (2002). Nat Rev Immunol, 2, 46-53.
- Kaysak P, Rasmussen R K, Causing C G, Bonni S, Zhu H, Thomsen G H and Wrana J L. (2000). Mol Cell, 6, 1365-1375.
- Konrad L, Scheiber J A, Völck-Badouin E, Keilani M M, Laible L, Brandt H, Schmidt A, Aumüller G and Hofmann R (2007) BMC Genomics 8: 318-330.
- Krishnaveni M S, Hansen J L, Seeger W, Morty R E, Sheikh S P, Eickelberg O. (2006). Biochem Biophys Res Commun. December 22; 351(3) 651-7

Massague J, Seoane J and Wotton D. (2005). Genes Dev, 19, 2783-2810.

Muraoka R S, Dumont N, Ritter C A, Dugger T C, Brantley D M, Chen J, Easterly E, Roebuck L R, Ryan S, Gotwals P J, Koteliansky V and Arteaga C L. (2002). J Clin Invest, 109, 1551-1559.

Nam J S, Suchar A M, Kang M J, Stuelten C H, Tang B, Michalowska A M, Fisher L W, Fedarko N S, Jain A, Pinkas J, Lonning S and Wakefield L M. (2006). Cancer Res, 66, 6327-6335.

Nikawa J. (1994). Gene November 18; 149 (2): 367-72.

Ogasa H, Noma T, Murata H, Kawai S, Nakazawa A (1996) Gene, 181: 185-190

Penafuerte C and Galipeau J. (2008). Cancer Immunol Immunother, 57, 1197-206.

Peng S B, Yan L, Xia X, Watkins S A, Brooks H B, Beight D, Herron D K, Jones M L, Lampe J W, McMillen W T, Mort N, Sawyer J S and Yingling J M. (2005). Biochemistry, 44, 2293-2304.

Rotzer D, Roth M, Lutz M, Lindemann D, Sebald W, Knaus P. (2001). EMBO J. February 1; 20 (3): 480-90.

Stagg J, Wu J H, Bouganim N and Galipeau J. (2004). Cancer Res, 64, 8795-8799.

Suzuki A, Shioda N, Maeda T, Tada M, Ueno N (1994) FEBS Lett 355: 19-22

Ulloa L, Doody J and Massague J. (1999). Nature, 397, 710-713.

---

The invention claimed is:

1. A conjugate protein comprising an interleukin-2 (IL-2) linked to a soluble TGF-beta type II receptor B (sTβRIIB); wherein the sTβRIIB is the ectodomain or extracellular domain of TGF-beta type II receptor B; wherein the conjugate protein comprises the sequence as shown in SEQ ID NO:2, 4, 6, 8 or a variant modified in a linker region between the IL-2 and the sTβRIIB; wherein the variant comprises a sequence having at least 95% similarity to SEQ ID NO:2, 4, 6, 8 and has the same activity as SEQ ID NO:2, 4, 6 or 8.

2. The conjugate protein according to claim 1, wherein the IL-2 is linked to the sTβRIIB by a peptide linker.

3. A pharmaceutical composition comprising the conjugate protein of claim 1 in admixture with a suitable diluent or carrier.

4. The conjugate protein according to claim 1, wherein the activity is selected from:

a. dominant negative inhibition of TGF-beta signaling pathway;

b. immunostimulation; and/or c. angiostatic properties.

* * * * *